United States Patent [19]
Ginsberg et al.

[11] Patent Number: 5,942,494
[45] Date of Patent: Aug. 24, 1999

[54] STIMULATION OF GENE EXPRESSION AND SYNTHESIS OF HEAT SHOCK PROTEIN 72/73 (HSP 70)

[75] Inventors: Henry N. Ginsberg, Scarsdale; Xujun Wu; Mingyue Zhou, both of New York, all of N.Y.

[73] Assignee: The Trustees of Columbia University in the City of New York, New York, N.Y.

[21] Appl. No.: 08/724,546

[22] Filed: Sep. 30, 1996

Related U.S. Application Data

[60] Provisional application No. 60/005,073, Oct. 6, 1995.
[51] Int. Cl.$^6$ ............................ A61K 38/00; A01H 35/00
[52] U.S. Cl. ............................ 514/18; 514/693; 514/12; 514/2; 530/331; 530/350
[58] Field of Search ........................ 530/350, 331; 514/2, 693, 18, 12

[56] References Cited

PUBLICATIONS

Cajone et al. Chemico–Biological Interactions 84(2) 97–112 Sep. 28, 1992.
Freeman et al. J. Cell. Physiol. 164(2):356–66 Aug. 1995.
Craig, E.A., B.K. Baxter, and J. Becker, J. Halladay, and T. Ziegelhotts, (1994) In: The Biology of Heat Shock Protein and Molecular Chaperone. pp. 31–52 Cold Spring Harbor Laboratory Press, Cold Spring Harbor, New York (Exhibit 1).
Currie, R.W., M. Karmazyn, M. Kloc, and K. Mailer, (1988) *Cir. Res.* 63:543–549. (Exhibit 2).
Morimoto, R.I., D.A. Jurvich, P.E. Kroeger, S.K. Mathus, S.P. Murply, A. Nakai, K. Sarge, K. Abravaya, and L.T. Sistonen, In: The Biology of Heat Shock Proteins and Molecular Chaperone, (1994) pp. 417–455. Cold Spring Harbor Laboratory Press. Cold Spring Harbor, New York (Exhibit 3).
Wang, X. et al. (1994) *Cell* 77:53–62. (Exhibit 4).
Abdella, P.M. et al. (1979) *Biochem. Biophys. Res. Commun.* 87(3): 734–742 (Exhibit 1).
Angelidis, C.E. et al. (1991) *Eur. J. Biochem.* 199(1):35–39 (Exhibit 2).
Ashburner, M. and Bonner, J.J. (1979) *Cell:* 17:241–254 (Exhibit 3).
Baler, R. et al. (1992) *J. Cell. Biol.* 117(6):1151–1159 (Exhibit 4).
Chomczynski, P. and Sacchi, N. (1987) *Anal. Biochem.* 167(1):156–159 (Exhibit 5).
Craig, E.A. (1985) *Crit. Rev. Biochem.* 18(3):239–280 (Exhibit 6).
Deshaies, R.J. et al. (1988) *Nature* 322(6167):800–805 (Exhibit 7).
Dierks, T. et al. (1993) *Phil. Trans. R. Soc. Lond. B* 339(1289): 335–341 (Exhibit 8).
Dixon, J.L. et al. (1991) *J. Biol. Chem.* 266(8):5080–5086 (Exhibit 9).
Dixon, J.L. and Ginsberg, H.N. (1993) *J. Lipid. Res.* 34(2): 167–179 (Exhibit 10).
Fenteany, G. et al. (1995) *Science* 268(5211):726–731 (Exhibit 11).
Freeman, M.L. (1993) *Radiation. Res.* 135(3):387–393 (Exhibit 12).
Gaitanaris, G.A. et al. (1990) *Cell* 61(6):1013–1020 (Exhibit 13).
Gething, M.–J. and Sambrook, J. (1992) *Nature* 355(6355):33–45 (Exhibit 14).
Goldberg, M.L. and Sarge, K.D. (1995) *Chem. & Biol.* 2(8):503–508 (Exhibit 15).
Goodson, M.L. and Sarge, K.D. (1995) *J. Biol. Chem.* 270(6): 2447–2450 (Exhibit 16).
Hartl, F.U., and Martin, J. (1992) *Annu. Rev. Biophys. Biomol. Struct.* 21:293–322 (Exhibit 17).
Hedge, R.S. et al. (1995) *J. Cell. Physiol.* 165(1):186–200 (Exhibit 18).
Hightower, L.E. (1991) *Cell* 66:191–197 (Exhibit 19).
Hiwasa, T. et al. (1990) *Carcinogenesis* 11(1):75–80 (Exhibit 20).
Inoue, S. et al. (1991) *J. Biol. Chem.* 266(20):13311–13317 (Exhibit 21).
King, R.W. et al. (1995) *Cell* 81(2):279–288 (Exhibit 22).
Landry, J. et al. (1991) *J. Cell. Physiol.* 147(1):93–101 (Exhibit 23).
Li, G.C. et al. (1991) *Proc. Natl. Acad. Sci. USA* 88:1681–1685 (Exhibit 24).
Lindquist, S. (1986) *Ann. Rev. Biochem.* 55:1151–1191 (Exhibit 25).
Liu, A.Y. et al. (1989) *J. Biol. Chem.* 264(20):12037–12045 (Exhibit 26).
Liu, H. et al. (1996) *J. Biol. Chem.* 271(9):4805–4812 (Exhibit 27).
Lowe, J. et al. (1995) *Science* 268(5210):533–539 (Exhibit 28).

(List continued on next page.)

*Primary Examiner*—Paula K. Hutzell
*Assistant Examiner*—Geetha P. Bansal
*Attorney, Agent, or Firm*—John P. White; Cooper & Dunham LLP

[57] ABSTRACT

This invention provides a method for increasing the level of heat shock protein in a cell which comprises contacting the cell with an effective amount of N-acetyl-leucyl-leucyl-norleucinal, so as to thereby increase the level of heat shock protein in the cell. This invention further provides a protein characterized by increased levels of the protein in a cell in response to contacting the cell with an effective amount of N-acetyl-leucyl-leucyl-norleucinal. This invention also provides a method for increasing the binding of apoprotein B100 to a heat shock protein in a cell. This invention provides a method of preserving an organ ex vivo, which comprises contacting the organ with an effective amount of N-acetyl-leucyl-leucyl-norleucinal. This invention also provides a method of preserving an organ in vivo, which comprises contacting the organ with an effective amount of N-acetyl-leucyl-leucyl-norleucinal.

22 Claims, 13 Drawing Sheets

OTHER PUBLICATIONS

Marber, M.S. et al. (1993). *Circulation* 88(3):1264–1272 (Exhibit 29).
Mitani, K. et al. (1993) *Bioch. J.* 290(3):819–825 (Exhibit 30).
Mosser, D.D. et al. (1988) *Molec. Cell. Biol.* 8(11):4736–4744 (Exhibit 31).
Neupert, W. and Pfanner, N. (1993) *Phil. Trans. R. Soc. Lond. B* 355–362 (Exhibit 32).
Ohtsuki, T. et al. (1992) *Brain Res.* 599(2):246–252 (Exhibit 33).
Pelham, H.R.B. (1986) *Cell* 46(7):959–961 (Exhibit 34).
Rabindran, S.K. et al. (1994) *Mol. Cell. Biol.* 14(10):6552–6560 (Exhibit 35).
Rabindran, S.K. et al. (1993) *Science* 259(5092):230–234 (Exhibit 36).
Radford, N.B. et al. (1996) *Proc. Natl. Acad. Sci. USA* 93(6): 2339–2342 (Exhibit 37).
Rock, K. L. et al. (1994) *Cell* 78(5):761–771 (Exhibit 38).
Sakata, N. et al. (1993) *J. Biol. Chem.* 268(31):(Exhibit 39).
Schissel, S.L. et al. (1995) *Biochemistry* 34:10463–10473 (Exhibit 40).
Sherwood, S.W. et al. (1993) *Proc. Natl. Acad. Sci. USA* 90(8): 3353–3357 (Exhibit 41).
Simon, M.M. et al. (1995) *J. Clin. Res.* 95(3):926–933 (Exhibit 42).
Ward, C.L. et al. (1995) *Cell* 83(1):121–127 (Exhibit 43).
Welch, W.J. and Feramisco, J.R. (1984) *J. Biol. Chem.* 259(7):4501–4513 (Exhibit 44).
Westwood, J.T. and Wu, C. (1993) *Molec. Cell. Biol.* 13(6): 3481–3486 (Exhibit 45).
Zafarullah, M. et al. (1993) *Exp. Cell. Res.* 208(2):371–377 (Exhibit 46).
Zhou, M.Y. et al. (1995) *J. Biol. Chem.* 270(42):25220–25224 (Exhibit 47).
Ginsberg, H.N. (1995) *Current Opin. Lipidol.* 6:275–280 (Exhibit 48).
Baler, R. et al. (1993) *Molec. Cell Biol.* 13(4):2486–2496 (Exhibit B).
Beckmann, R.P. et al. (1990) *Science* 248:850–854 (Exhibit C).
Hayes, S.A. and Dice, J.F. (1996) *J. Cell Biol.* 132(3):255–258 (Exhibit D).
Plumier, J.–C., L. et al. (1995) *J. Clin. Invest.* 95:1854–1860 (Exhibit H).
Sarge, K.D. et al. (1993) *Molec. Cell. Biol.* 13:1392–1407 (Exhibit I).
Johnson, A.J. et al. (1995) *Arterio. Thromb. Vasc. Biol.* 15(1):27–36 (Exhibit E).
Marber, M.S. et al. (1995) *J. Clin. Invest.* 95:1446–1456 (Exhibit F).
Minowada, G. and Welch, W.J. (1995) *J. Clin. Invest.* 95:3–12 (Exhibit G).

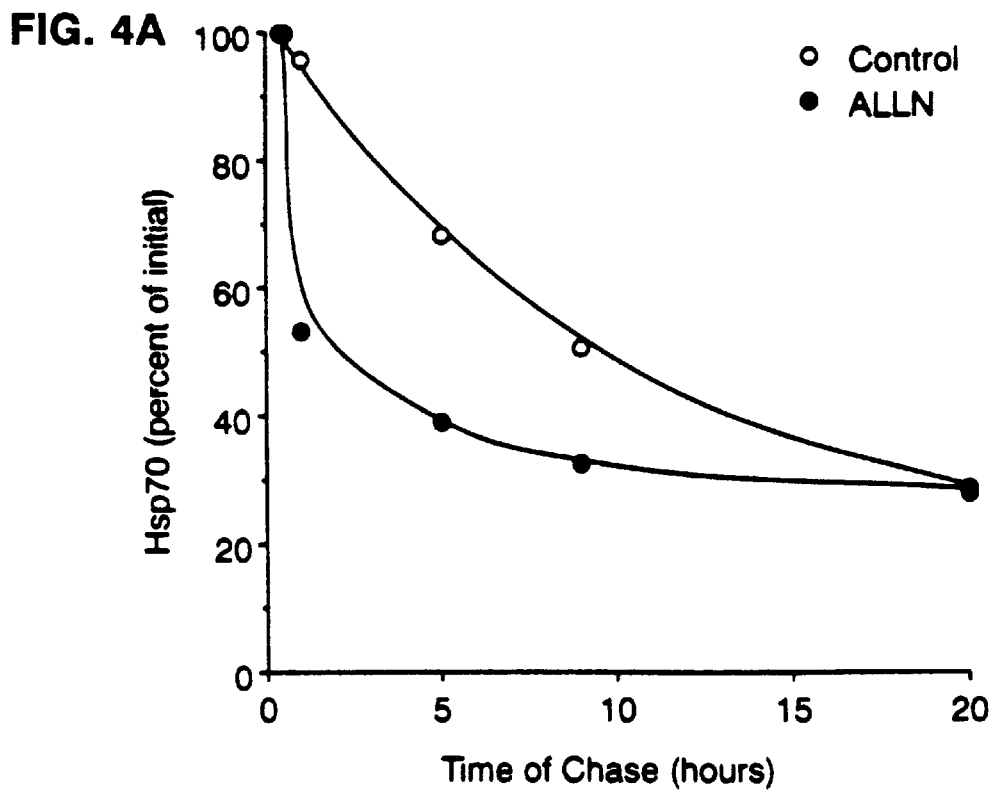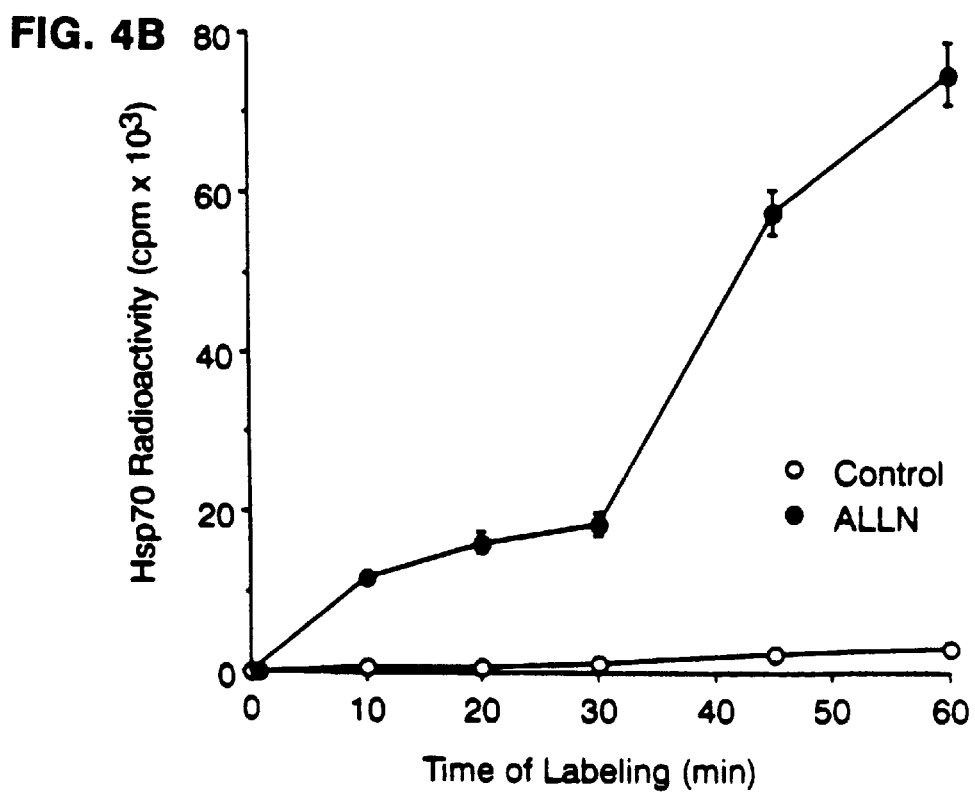

FIG. 6A
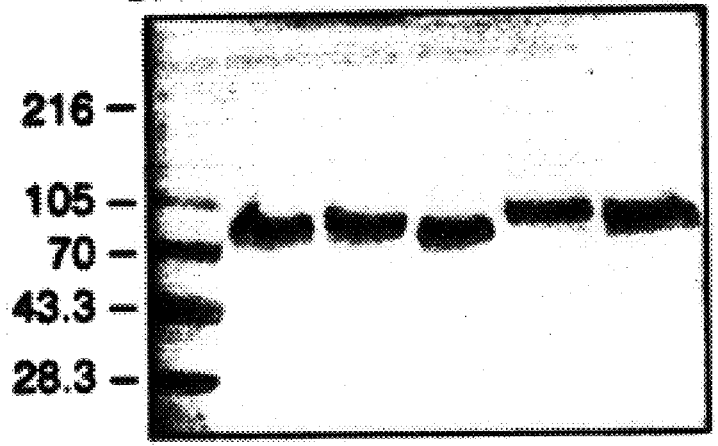
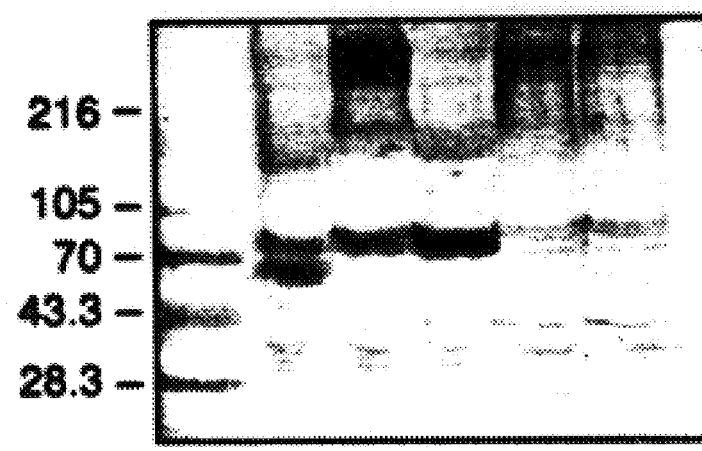
FIG. 6B

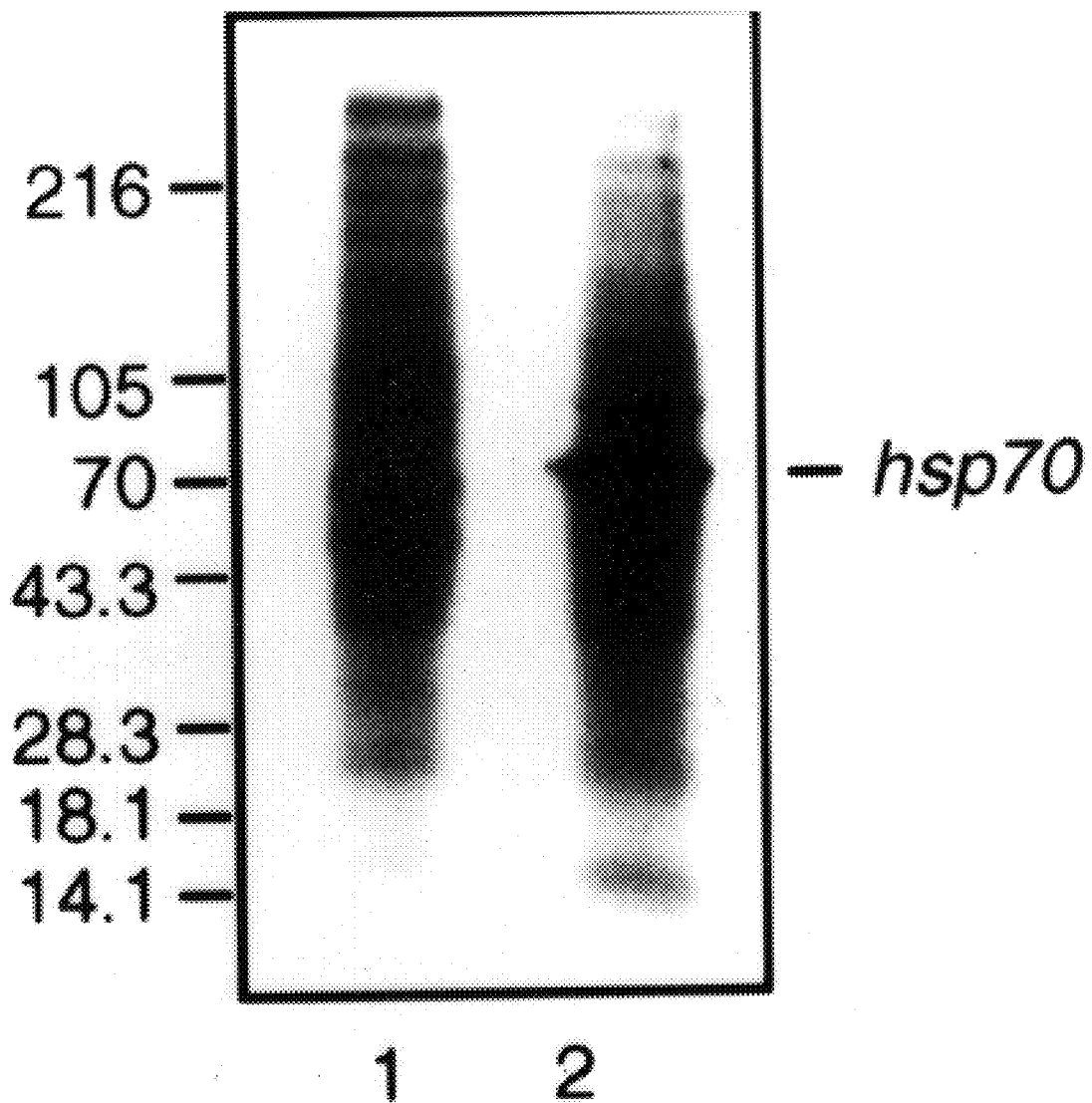

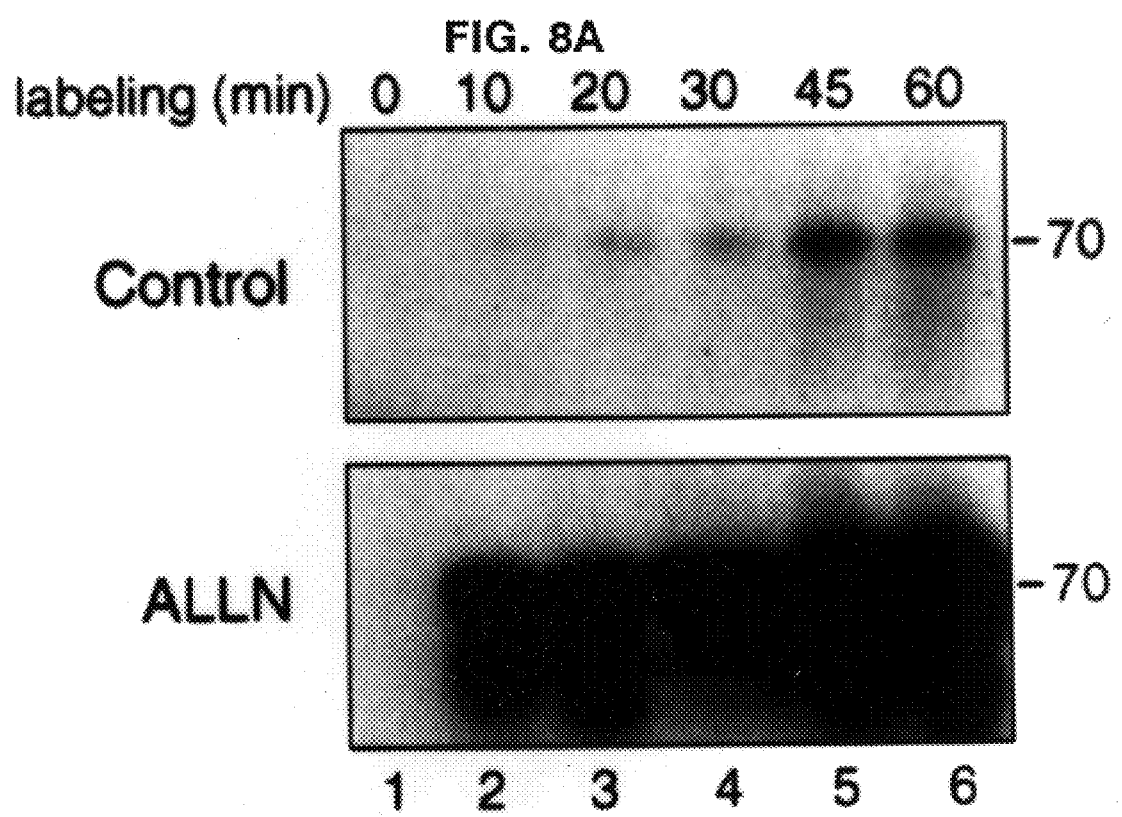

STIMULATION OF GENE EXPRESSION AND SYNTHESIS OF HEAT SHOCK PROTEIN 72/73 (HSP 70)

CROSS-REFERENCE TO RELATED APPLICATIONS

This application claims the benefit of copending U.S. Provisional Application Ser. No. 60/005,073, filed Oct. 6, 1995.

STATEMENT REGARDING FEDERALLY FUNDED RESEARCH

The invention disclosed herein was made with Government support under NHLBI, NIH Grant No. HL 36000 from the Public Health Service and NIH Grant No. HL 21007. Accordingly, the U.S. Government has certain rights in this invention.

Throughout this application, various references are referred to within parentheses. Disclosures of these publications in their entireties are hereby incorporated by reference into this application to more fully describe the state of the art to which this invention pertains. Full bibliographic citation for these references may be found at the end of this application, preceding the claims.

BACKGROUND OF THE INVENTION

Heat shock protein 72/73 (Hsp70) is a cytosolic molecular chaperone that carrys out fundamental roles under both normal and stress situations. There is great interest in delineating the mechanisms whereby Hsp70 levels are regulated. Here it is demonstrated that N-acetyl-leucyl-leucyl-norleucinal (ALLN), a synthetic tripeptide which inhibits cysteine proteases and inhibits proteasomes, can markedly induce Hsp70 levels (up to 30-fold above baseline in HepG2 cells and human endothelial cells). Induction of Hsp70 by ALLN is dose-dependent and not related to cell toxicity. ALLN selectively increases Hsp70 levels without affecting Hsp25, Hsp27, Hsp60, Hsp86, Hsp90, Hsp104 or immunoglobulin heavy chain binding protein (Bip) in HepG2 cells. A series of other protease inhibitors that were examined had no effect on Hsp70, except for N-acetyl-leucyl-leucyl-methioninal (ALLM), which is highly similar to ALLN both in its structure and protease inhibitory features. ALLN induces Hsp70 not only by stabilizing the protein but also by dramatically increasing its synthesis. The modulation of Hsp70 synthesis by ALLN appears to result from a rapid and marked increase in transcription of the hsp70, i.e., hsp72 gene, since the induction of hsp70, i.e. hsp72, mRNA was blocked in cells co-treated with actinomycin D. hsp70 (i.e. hsp72) mRNA levels are affected by the duration of exposure to ALLN: significant elevations occur within 60 min. of treatment, and a decline to background levels is observed by 7 hours of recovery. The ALLN-induced increase in hsp70 (i.e. hsp72) gene expression is associated with trimerization of the heat shock transcriptional factor (HSF1). ALLN does not affect the steady-state HSF1 protein level. The effects of ALLN appear to require de novo protein synthesis, since the induction of both HSF1 trimerization and hsp70 (i.e. hsp72) transcription is blocked by co-treatment with cycloheximide. These results suggest that a cysteine protease may be involved in the regulation of Hsp70 synthesis via effects on the hsp70 transcriptional factor, HSF1. This cysteine protease may normally degrade a rapidly turning-over protein involved in the trimerization of HSF. Of a series of protease inhibitors that were tested, only the related aldehydic tripeptides, N-acetyl-leucyl-leucyl-methioninal (ALLM) and the proteasome inhibitor, Cbz-leucyl-leucyl-leucinal (MG132) induced Hsp70 levels. The specific proteasome inhibitor, lactacystin, which has a different structure, also induced Hsp70 levels. Overall, these results suggest that a rapidly turning-over protein which is normally degraded by proteasomes may be involved in the regulation of Hsp70 synthesis via effects on the hsp70 transcriptional factor, HSF1.

Induction of heat shock (stress) proteins (Hsps), a class of molecular chaperones is a physiological and biochemical response to an abrupt increase in temperature (Ashburner, et al., 1979; Lindquist, 1986) and to a variety of other metabolic insults (Craig, 1985; Morimoto, et al., 1994), including exposure to heavy metals, amino acid analogs, toxins and oxidative stress. This response is found in all prokaryotic and eukaryotic cells and is characterized by a repression of normal protein synthesis together with the rapid initiation of transcription of several Hsp-encoding genes (Lindquist, 1986). Among these highly conserved Hsp family members are two nearly identical, cytosolically located heat shock proteins, Hsp72 (the inducible form) and Hsp73 (the constitutively synthesized form). These two proteins, commonly referred to as cytosolic Hsp70, function as molecular chaperones and play fundamental roles in a number of important biological processes. Under nonstressed conditions, Hsp70 interacts transiently with nascent polypeptides to facilitate proper folding and maturation and to promote protein translocation across mitochondrial and endoplasmic reticulum (ER) membranes (Hartl and Martin, 1992; Deshaies, et al., 1988; Dierks, et al., 1993; Neupert and Pfanner, 1993). During stress conditions, Hsp70 forms a complex with proteins that misfold or unfold, thus either "rescuing" these proteins from irreversible damage or degradation (Hightower, 1991; Gaitanaris, et al., 1991; Gething and Sambrook, 1992; Craig, et al., 1994) or increasing their susceptibility to proteolytic attack (Hayes and Dice, 1996).

Recently, elevated expression of Hsp70 and other Hsps has been observed in cells and tissues under conditions representative of human diseases, including ischemia, oxidant injury, atherosclerosis and aging (Marber, et al., 1988; Minowada and Welch, 1995; Johnson, et al., 1995). The increased expression of these stress proteins could represent an acute response to altered physiological states, as well as chronic adaption to particular diseases. The primary function of these stress responses is thought to be cytoprotective. For example, overexpression of Hsp70 alone was demonstrated to protect cells from thermal injury and to increase cell survival (Angelidis, et al., 1991; Li, et al., 1991). Elevated levels of inducible Hsp70 have been associated with improved post-ischemic recovery (Currie, et al., 1988) and tolerance to ischemia in gerbil hippocampal neurons (Ohtsuki, et al., 1992). It has also been reported that both heat shock-induced and exogeneous Hsp70 can protect smooth muscle cells from serum deprivation-induced cell death (Johnson, et al., 1995). Overexpression of Hsp70 also protects murine fibroblasts from both ultraviolet (UV)-light injury and proinflammatory cytokines released during UV-exposure (Simon, et al., 1995). The protective role of Hsp70 was demonstrated clearly by two recent studies with transgenic mice in which overexpression of human inducible Hsp70 protected myocardium from ischemic reperfusion injury (Marber, et al., 1995; Plumier, et al., 1995) and enhanced postischemic recovery of the intact heart (Rodford, et al., 1996). These potential clinical applications of Hsp70 have stimulated investigators to search for efficient pharmacological means of rapidly and selectively inducing Hsp70.

Studies of the involvement of molecular chaperones in the assembly and secretion of apolipoprotein B100 (apoB)-containing lipoprotein from cultured liver (HepG2) cells have been performed. ApoB is a very large, extremely hydrophobic secretory protein that appears to be constitutively translated but inefficiently translocated across the ER membranes (Dixon and Ginsberg, 1993; Ginsberg, 1995). As a result, nascent apoB assumes a transmembrane topology with some portion of the nascent protein exposed to the cytosol. Since the extreme hydrophobicity of apoB makes it unlikely that it would maintain a translocation-competent conformation in the cytosol without the "assistance" of a chaperone, a possible association of apoB with Hsp70 was investigated (Zhou, et al., 1995). It was found that Hsp70 associated transiently with nascent apob and that this interaction appeared to be regulated by the translocation status of apoB. Less apoB was bound to Hsp70 in the presence of oleic acid, which facilitates apoB translocation across the ER membranes by stimulating new triglyceride synthesis. In contrast, more apoB was bound to Hsp70 in the presence of a cysteine protease inhibitor, N-acetylleucyl-leucyl-norleucinal, (ALLN), which is also a proteasome inhibitor (Rock, et al., 1994; and Ward, et al., 1995), which protects apoB from degradation without enhancing translocation. During these studies, a marked, unexpected increase in Hsp70 levels in cells treated with ALLN was observed. The studies presented here were designed to determine the mechanisms underlying the induction of Hsp70 by ALLN.

SUMMARY OF THE INVENTION

This invention provides a method for increasing the level of Heat Shock Protein in a cell which comprises contacting the cell with an effective amount of an inhibitor which inhibits the cysteine protease which cleaves the same bond as the cysteine protease inhibited by N-acetyl-leucyl-leucyl-norleucinal, so as to thereby increase the level of Heat Shock Protein in the cell.

This invention also provides a method for increasing the level of Heat Shock Protein in a cell which comprises contacting the cell with an effective amount of a proteasome inhibitor which inhibits a proteasome, so as to thereby increase the level of Heat Shock Protein in the cell.

This invention further provides a method for increasing the level of Heat Shock Protein in a subject which comprises administering to the subject an effective amount of an inhibitor which inhibits the cysteine protease which cleaves the same bond as the cysteine protease inhibited by N-acetyl-leucyl-leucyl-norleucinal, so as to thereby increase the level of Heat Shock Protein in the subject.

This invention provides a method for increasing the level of Heat Shock Protein in a subject which comprises administering to the subject an effective amount of a pharmaceutical composition comprising an effective amount of an inhibitor which inhibits the cysteine protease which cleaves the same bond as the cysteine protease inhibited by N-acetyl-leucyl-leucyl-norleucinal, and a pharmaceutically acceptable carrier, so as to thereby increase the level of Heat Shock Protein in the subject.

This invention provides a method for increasing the level of Heat Shock Protein in a subject which comprises administering to the subject an effective amount of an inhibitor which inhibits a proteasome, so as to thereby increase the level of Heat Shock Protein in the subject.

This invention provides a method for increasing the amount of a complex between apoprotein B100 and heat shock protein in a cell, which comprises contacting the cell with an effective amount of a inhibitor which inhibits the cysteine protease which cleaves the same bond as the cysteine protease inhibited by N-acetylleucyl-leucyl-norleucinal, so as to increase the amount of the complex between apoprotein B100 and heat shock protein in the cell.

This invention provides a method for increasing the amount of a complex between apoprotein B100 and heat shock protein in a cell, which comprises contacting the cell with an effective amount of a proteasome inhibitor which inhibits a proteasome, so as to increase the amount of the complex between apoprotein B100 and heat shock protein in the cell. This invention provides a protein characterized by increased levels of the protein in a cell in response to contacting the cell with an effective amount of an inhibitor which inhibits the cysteine protease which cleaves the same bond as the cysteine protease inhibited by N-acetyl-leucyl-leucyl-norleucinal.

This invention provides a protein characterized by increased levels of the protein in a cell in response to contacting the cell with an effective amount of a proteasome inhibitor.

This invention provides a pharmaceutical composition comprising an effective amount of an inhibitor which inhibits the cysteine protease which cleaves the same bond as the cysteine protease inhibited by N-acetylleucyl-leucyl-norleucinal, and a pharmaceutically acceptable carrier.

This invention provides a pharmaceutical composition comprising an effective amount of an inhibitor which inhibits a proteasome, and a pharmaceutically acceptable carrier.

This invention provides a method of treating an abnormality in a subject which is alleviated by increasing the level of a heat shock protein, which comprises administering to the subject an effective amount of an inhibitor which inhibits the cysteine protease which cleaves the same bond as the cysteine protease inhibited by N-acetyl-leucyl-leucyl-norleucinal, so as to increase the level of the heat shock protein, thereby treating the abnormality.

This invention provides a method of treating an abnormality in a subject which is alleviated by increasing the level of a heat shock protein, which comprises administering to the subject an effective amount of an inhibitor which inhibits a proteasome, so as to increase the level of the heat shock protein, thereby treating the abnormality.

This invention provides a method of treating an abnormality in a subject which is alleviated by increasing the binding of apoprotein B100 to a heat shock protein in the subject which comprises administering to the subject an effective amount of an inhibitor, which inhibits the cysteine protease which cleaves the same bond as the cysteine protease inhibited by N-acetylleucyl-leucyl-norleucinal, so as to increase the binding of apoprotein B100 to a heat shock protein, thereby treating the abnormality.

This invention provides a method of treating an abnormality in a subject which is alleviated by increasing the binding of apoprotein B100 to a heat shock protein in the subject which comprises administering to the subject an effective amount of an inhibitor which inhibits a proteasome, so as to increase the binding of apoprotein B100 to a heat shock protein, thereby treating the abnormality.

This invention provides a method of treating an abnormality in a subject which is alleviated by selectively increasing the level of a heat shock protein, which comprises administering to the subject an effective amount of the pharmaceutical composition comprising an effective amount of an inhibitor which inhibits the cysteine protease which cleaves the same bond as the cysteine protease inhibited by N-acetyl-leucyl-leucylnorleucinal, and a pharmaceutically acceptable carrier, thereby treating the abnormality.

This invention provides a method of treating an abnormality in a subject which is alleviated by selectively increasing the level of a heat shock protein, which comprises administering to the subject an effective amount of a pharmaceutical composition comprising an effective amount of an inhibitor which inhibits a proteasome, and a pharmaceutically acceptable carrier, thereby treating the abnormality.

This invention provides a method of preserving organs ex vivo, which comprises contacting the organ with an effective amount of an inhibitor which inhibits the cysteine protease which cleaves the same bond as the cysteine protease inhibited by N-acetyl-leucyl-leucyl-norleucinal, so as to increase the level of Heat Shock Protein 70, thereby preserving the organ.

This invention provides a method of preserving organs ex vivo, which comprises contacting the organ with an effective amount of an inhibitor which inhibits a proteasome, so as to increase the level of Heat Shock Protein 70, thereby preserving the organ.

This invention provides a method of preserving organs in vivo, which comprises contacting an effective amount of an inhibitor which inhibits the cysteine protease which cleaves the same bond as the cysteine protease inhibited by N-acetyl-leucyl-leucyl-norleucinal, with the organ, so as increase the level of Heat Shock Protein 70, thereby preserving the organ.

This invention provides a method of preserving organs in vivo, which comprises contacting an effective amount of an inhibitor which inhibits a proteasome, so as increase the level of Heat Shock Protein 70, thereby preserving the organ.

This invention provides a method of producing Heat Shock Protein 70, which comprises: (a) inserting nucleic acid encoding the Heat Shock Protein 70 into a suitable vector;

(b) inserting the resulting vector into a suitable host cell, so as to obtain a cell which expresses the nucleic acid which produces the Heat Shock Protein 70 ; (c) contacting a plurality of cells from step (b) with an inhibitor which inhibits the cysteine protease which cleaves the same bond as the cysteine protease inhibited by N-acetyl-leucyl-leucyl-norleucinal; (d) recovering the Heat Shock Protein 70 produced by the cells; and (e) purifying the Heat Shock Protein 70 so recovered.

This invention provides a method of producing Heat Shock Protein 70, which comprises: (a) inserting nucleic acid encoding the Heat Shock Protein 70 into a suitable vector;

(b) inserting the resulting vector into a suitable host cell, so as to obtain a cell which expresses the nucleic acid which produces the Heat Shock Protein 70 ; (c) contacting a plurality of cells from step (b) with an inhibitor which inhibits a proteasome, so as to increase the level of Heat Shock Protein 70 ; (d) recovering the Heat Shock Protein 70 produced by the cells; and (e) purifying the Heat Shock Protein 70 so recovered.

This invention provides a method of producing the protein characterized by increased levels of the protein in a cell in response to contacting the cell with an effective amount of an inhibitor which inhibits the cysteine protease which cleaves the same bond as the cysteine protease inhibited by N-acetyl-leucyl-leucyl-norleucinal, which comprises: (a) inserting nucleic acid encoding the protein, into a suitable vector; (b) inserting the resulting vector into a suitable host cell, so as to obtain a cell which expresses the nucleic acid which produces the protein; (c) contacting a plurality of cells from step (b) with an inhibitor which inhibits the cysteine protease which cleaves the same bond as the cysteine protease inhibited by N-acetyl-leucyl-leucyl-norleucinal; (d) recovering the protein produced by the cells of step (c); and (e) purifying the protein so recovered.

This invention provides a method of producing the protein characterized by increased levels of the protein in a cell in response to contacting the cell with an effective amount of a proteasome inhibitor, which comprises: (a) inserting nucleic acid encoding the protein, into a suitable vector;

(b) inserting the resulting vector into a suitable host cell, so as to obtain a cell which expresses the nucleic acid which produces the protein; (c) contacting a plurality of cells from step (b) with an inhibitor which inhibits a proteasome, so as to increase the level of Heat Shock Protein 70 ; (d) recovering the protein produced by the cells of step (c); and (e) purifying the protein so recovered.

BRIEF DESCRIPTION OF THE FIGURES

FIGS. 4A–4B: Effects of ALLN on Hsp70 turnover and synthesis rates in HepG2 cells. Confluent culture dishes were preincubated for 4 hours with serum-free MEM containing either 1.5% BSA alone (Control) or BSA plus 40 µg/ml of ALLN (ALLN). (A) The preincubated cells were radiolabeled with 3H-leucine (150 µCi/ml) in serum-free, leucine-free medium with/without ALLN for 20 min., washed 3 times with medium free of isotope and then chased in serum-free medium containing BSA with/without ALLN for up to 20 hours. At the indicated time points, cells were harvested and lysed. Samples were immediately stored in a −80° C. freezer. Immunoprecipitation of Hsp70 was performed as described in FIG. 1. Data at each time point were presented as means of cpm from duplicate dishes. (B) . The preincubated cells were radiolabeled with 3H-leucine (150 µCi/ml) in the presence/absence of ALLN for the indicated periods of time. Cells were then subjected to lysis and immunoprecipitation as described above. All values were presented as means ± SD from three individual dishes.

FIGS. 6A–6B: ALLN affects the trimerization of HSF. HepG2 cells were treated with serum-free MEM containing 1.5% BSA for 2 hours at 37° C. without any additions (lane1), at 37 ° C. but containing 40µg/ml of ALLN in the medium (lane2), at 37° C. in a medium containing both ALLN and 50 µg/ml of cycloheximide (lane3) , at 42° C. alone (lane4), or at 42° C. plus cycloheximide in the medium (lane5). Cell lysates were prepared as described under Experimental Details. The lysates were either directly run on the SDS-PAGE (A) to show the steady-state protein levels of HSF1 or subjected to cross-linking with ethylene glycol bis sucrinimidylsuccinate (EGS) before running the gel (B) to show the oligomeric forms of HSF1. The proteins were then transfered to a nitrocellulose membrane and immunoblotted with anti-human HSF1 antibody. Arrows on the right side indicates the monomeric, dimeric or trimeric forms of HSF1, respectively. This experiment was repeated three times with identical results.

FIGS. 7A–7B: Effects of ALLN on the biosynthesis of other members of Hsp family and related proteins. HepG2 cells were pre-treated and radiolabeled with or without ALLN for 4 hours as described in FIG. 1. Cell lysates were used for SDS-PAGE (A), or for immunoprecipitation with anti-Hsp25, -Hsp27, -Hsp60, -Hsp70, -Hsp86, -Hsp90, -Hsp104, -Bip, or -albumin antibodies respectively (1 µg/ml) (B). Because the anti-Hsp25, -Hsp27, -Hsp60 and Hsp90 antibodies are from a rat source, rabbit anti-rat IgG antibody was added after the first incubation, and the incubation was extended for another 1 hour at 4° C. before collection with protein A-Sepharose. Immunoprecipitates were loaded for SDS-PAGE and aliquoted for scintillation counting and plotting. Each value was presented as mean ±S.D. from three individual culture dishes.

FIGS. 8A–8C: Effects of ALLN on Hsp70 synthesis and turnover rates in HepG2 cells. Confluent culture dishes were preincubated for 4 hours with serum-free MEM containing either 1.50% BSA alone (Control) or BSA plus 40 µg/ml of ALLN (ALLN). (A and B): The preincubated cells were radiolabeled with [$^3$H]-leucine (150 µCi/ml) in the presence or absence of ALLN for the indicated periods of time. Cells were then subjected to lysis and immunoprecipitation with anti-Hsp70 antibody as described in FIG. 1. Immunoprecipitates were analyzed on SDS-PAGE and fluorography (A) and also aliquoted for scintillation counting (B). Each value was presented as means ± S.D. from three individual dishes. (C): The preincubated cells were radiolabeled with [$^3$H] -leucine (150 µCi/ml) in serum-free, leucine-free medium with or without ALLN for 20 min, washed 3 times with medium free of isotope and then chased in serum-free medium containing BSA with or without ALLN for different periods of time. At the indicated time points, cells were harvested and lysed. Immunoprecipitation of Hsp70 was performed as described above. Data at each time point were presented as means of cpm from duplicate dishes. Similar results were obtained in two separate experiments for both studies.

DETAILED DESCRIPTION OF THE INVENTION

Figure 1A:
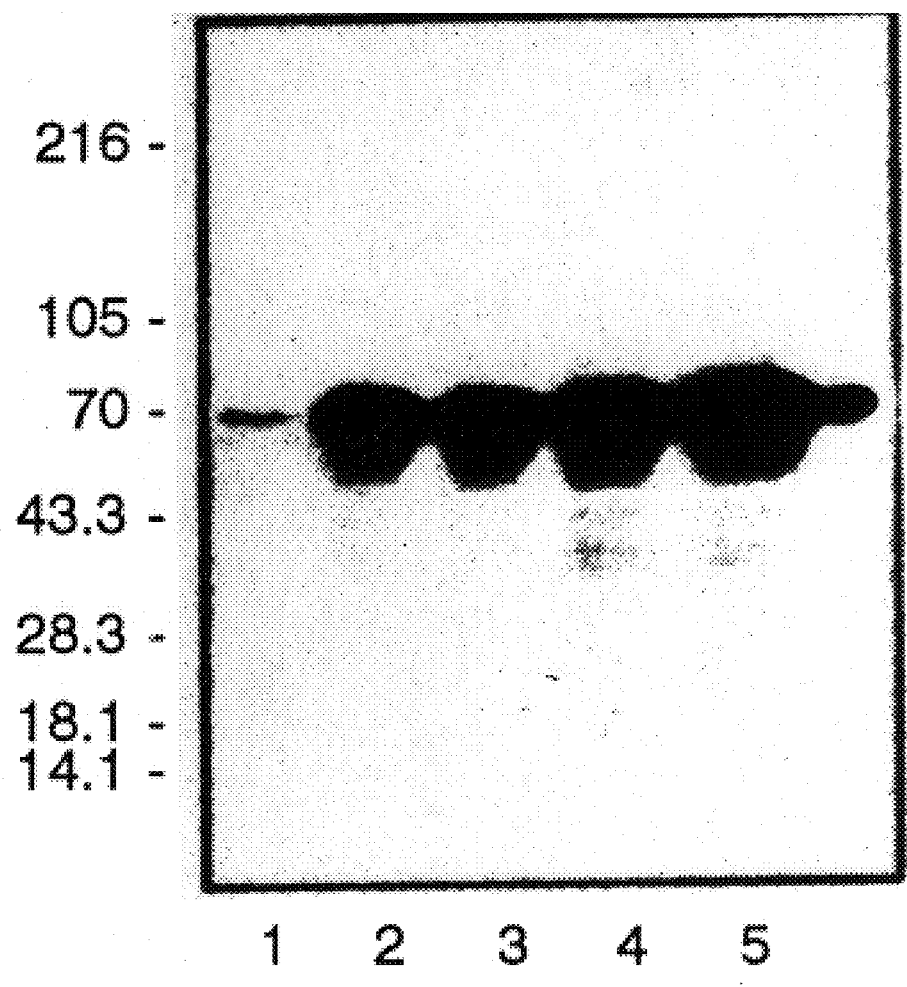
FIG. 1A–1C: Dose-dependent induction of Hsp70 by ALLN in human hepatoma cell line HepG2 cells. HepG2 cells were grown up to 95% confluence and then preincubated for 4 hours in a 37° C. incubator with serum-free minimum essential medium (MEM), followed by radiolabeling with 3H-leucine (150 $\mu$Ci/ml) dissolved in serum-free, leucine-free medium. Preincubation and labeling medium each contained 1.5% bovine serum albumin (BSA) plus different concentrations of ALLN as indicated. After labeling, cells were collected and lysed, and Hsp70 was immunoprecipitated under denaturing conditions as described under Experimental Details. Cell lysates containing an equal amount of TCA-insoluble radioactivity were used for immunoprecipitation. (A): The immunoprecipitates were analyzed by sodium dodecyl sulfate-polyacryamide gel electrophoresis (SDS-PAGE) and fluorography. Numbers on the left-hand side denote molecular markers. (B): The Hsp70 radioactivity was quantitated by scintillation counting and plotted. All the values were presented as means ± SD from three individual culture dishes.

This invention provides a method for increasing the level of Heat Shock Protein in a cell which comprises contacting the cell with an effective amount of an inhibitor which inhibits the cysteine protease which cleaves the same bond as the cysteine protease inhibited by N-acetyl-leucyl-leucyl-norleucinal, so as to thereby increase the level of Heat Shock Protein in the cell. In a preferred embodiment of the invention the heat shock protein is Heat Shock Protein 70. In a further preferred embodiment the Heat Shock Protein 70 is Heat Shock Protein 72. In a preferred embodiment of the invention the inhibitor is an aldehydic tripeptide. In a more preferred embodiment the aldehydic tripeptide is N-acetyl-leucyl-leucyl-methioninal. In another preferred embodiment the aldehydic tripeptide is N-acetyl-leucylleucyl-methioninal.

Heat Shock Protein 70 is the generic term for two proteins: Hsp72 and Hsp73. As used herein, Heat Shock Protein 70 is defined as Heat Shock Protein 72, Hsp72, the inducible form of Heat Shock Protein 70. Similarly, the gene which encodes for the inducible form of Hsp70, Hsp72, is generically named as hsp70 and is more specifically named as hsp72.

This invention provides a method for increasing the level of Heat Shock Protein in a cell which comprises contacting the cell with an effective amount of a proteasome inhibitor which inhibits a proteasome, so as to thereby increase the level of Heat Shock Protein in the cell. In a preferred embodiment of the invention the proteasome inhibitor is an aldehydic tripeptide. In one embodiment the aldehydic tripeptide is N-acetyl-leucyl-leucyl-norleucinal. In another embodiment the aldehydic tripeptide is N-acetyl-leucyl-leucyl-methioninal. In a still further embodiment the aldehydic tripeptide is Cbz-leucyl-leucyl-leucinal. In a preferred embodiment of the invention the proteasome inhibitor is lactacystin.

As used herein, proteasome is defined as a multicatalytic ptoteolytic organelle that is made of multiple subunits of a protein. The proteasome appears to be a major site of degradation for cytosolic proteins.

This invention provides a method for increasing the level of Heat Shock Protein in a subject which comprises administering to the subject an effective amount of an inhibitor which inhibits the cysteine protease which cleaves the same bond as the cysteine protease inhibited by N-acetyl-leucyl-leucyl-norleucinal, so as to thereby increase the level of Heat Shock Protein in the subject.

This invention provides a method for increasing the level of Heat Shock Protein in a subject which comprises administering to the subject an effective amount of a pharmaceutical composition comprising an effective amount of an inhibitor which inhibits the cysteine protease which cleaves the same bond as the cysteine protease inhibited by N-acetyl-leucyl-leucyl-norleucinal, and a pharmaceutically acceptable carrier, so as to thereby increase the level of Heat Shock Protein in the subject. In a preferred embodiment of either of these methods the heat shock protein is Heat Shock Protein 70. In a further preferred embodiment the Heat Shock Protein 70 is Heat Shock Protein 72. In a preferred embodiment the inhibitor is an aldehydic tripeptide. In a more preferred embodiment the aldehydic tripeptide is N-acetyl-leucyl-leucyl-norleucinal. In another preferred embodiment the aldehydic tripeptide is N-acetyl-leucylleucyl-methioninal. The subject may be a mammal or a human subject.

This invention provides a method for increasing the level of Heat Shock Protein in a subject which comprises administering to the subject an effective amount of an inhibitor which inhibits a proteasome, so as to thereby increase the level of Heat Shock Protein in the subject. In a preferred embodiment the heat shock protein is Heat Shock Protein 70. In a further preferred embodiment the Heat Shock Protein 70 is Heat Shock Protein 72. In a preferred embodiment the proteasome inhibitor is an aldehydic tripeptide. In a preferred embodiment the aldehydic tripeptide is N-acetyl-leucyl-leucyl-norleucinal. In another preferred embodiment the aldehydic tripeptide is N-acetyl-leucyl-leucyl-methioninal. In another preferred embodiment the aldehydic tripeptide is Cbz-leucyl-leucyl-leucinal. In another preferred embodiment the proteasome inhibitor is lactacystin. The subject may be a mammal or a human subject.

This invention provides a method for increasing the amount of a complex between apoprotein B100 and heat shock protein in a cell, which comprises contacting the cell with an effective amount of a inhibitor which inhibits the cysteine protease which cleaves the same bond as the cysteine protease inhibited by N-acetylleucyl-leucyl-norleucinal, so as to increase the amount of the complex between apoprotein B100 and heat shock protein in the cell. In a preferred embodiment the heat shock protein is Heat Shock Protein 70. In a further preferred embodiment the Heat Shock Protein 70 is Heat Shock Protein 72. In a preferred embodiment the inhibitor is an aldehydic tripeptide. The aldehydic tripeptide may be N-acetyl-leucyl-leucyl-norleucinal or N-acetyl-leucyl-leucyl-methioninal.

This invention provides a method for increasing the binding of apoprotein B100 to a heat shock protein in a cell, which comprises contacting the cell with an effective amount of a proteasome inhibitor which inhibits a proteasome, so as to increase the binding of apoprotein B100 to a heat shock protein in a cell. In a preferred embodiment the heat shock protein is Heat Shock Protein 70. In a further preferred embodiment the Heat Shock Protein 70 is Heat Shock Protein 72. In a preferred embodiment the proteasome inhibitor is an aldehydic tripeptide. In a still further embodiment the aldehydic tripeptide may be N-acetyl-leucyl-leucyl-norleucinal, N-acetyl-leucyl-leucyl-methioninal, or Cbz-leucyl-leucyl-leucinal. In a preferred embodiment the proteasome inhibitor is lactacystin.

This invention provides a protein characterized by increased levels of the protein in a cell in response to contacting the cell with an effective amount of an inhibitor which inhibits the cysteine protease which cleaves the same bond as the cysteine protease inhibited by N-acetyl-leucyl-leucyl-norleucinal. In an embodiment of the invention the protein is further characterized by being a rapidly turning over protein. In an embodiment the increased levels of the protein increase levels of heat shock protein. In a preferred embodiment the heat shock protein is Heat Shock Protein 70. In a further preferred embodiment the Heat Shock Protein 70 is Heat Shock Protein 72. In an embodiment the protein is characterized by being of a molecular weight of 80–90 kDa. In a preferred embodiment the inhibitor is an aldehydic tripeptide. In a further preferred embodiment the aldehydic tripeptide may be N-acetyl-leucyl-leucyl-norleucinal or N-acetyl-leucyl-leucyl-methioninal. This invention provides an isolated antibody directed to the protein characterized by increased levels of the protein in a cell in response to contacting the cell with an effective amount of the inhibitor. This invention provides an isolated antibody directed to the 80–90 kDa protein . In one embodiment the antibody is a polyclonal antibody. In another embodiment the antibody is a monoclonal antibody.

This invention provides a protein characterized by increased levels of the protein in a cell in response to contacting the cell with an effective amount of a proteasome inhibitor. In an embodiment the protein is characterized by being degraded by proteasomes in nonstress conditions. In a preferred embodiment the poteasome inhibitor is an aldehydic tripeptide. In a further preferred embodiment the aldehydic tripeptide may be N-acetyl-leucyl-leucyl-norleucinal, N-acetyl-leucyl-leucyl-methioninal, or Cbz-leucyl-leucyl-leucinal. In a preferred embodiment the poteasome inhibitor is lactacystin. This invention provides an isolated antibody directed to the protein characterized by increased levels of the protein in a cell in response to contacting the cell with an effective amount of a proteasome inhibitor. In one embodiment the antibody is a polyclonal antibody. In another embodiment the antibody is a monoclonal antibody.

This invention provides a pharmaceutical composition comprising an effective amount of an inhibitor which inhibits the cysteine protease which cleaves the same bond as the cysteine protease inhibited by N-acetyl-leucyl-leucyl-norleucinal, and a pharmaceutically acceptable carrier. In a preferred embodiment of the invention the inhibitor is an aldehydic tripeptide. In a further preferred embodiment the aldehydic tripeptide is N-acetyl-leucyl-leucyl-norleucinal or N-acetyl-leucyl-leucyl-methioninal.

This invention provides a pharmaceutical composition comprising an effective amount of an inhibitor which inhibits a proteasome, and a pharmaceutically acceptable carrier. In a preferred embodiment of the invention the proteasome inhibitor is an aldehydic tripeptide. In a further preferred embodiment the aldehydic tripeptide is N-acetyl-leucyl-leucyl-norleucinal, N-acetyl-leucyl-leucyl-methioninal, or Cbz-leucyl-leucyl-leucinal. In a preferred embodiment of the invention the proteasome inhibitor is lactacystin.

The invention also provides a pharmaceutical composition comprising an effective amount of the inhibitors described above and a pharmaceutically acceptable carrier. In the subject invention an "effective amount" is any amount of an inhibitor which, when administered to a subject suffering from a disease or abnormality against which the inhibitors are effective, causes reduction, remission, or regression of the disease or abnormality. In the practice of this invention the "pharmaceutically acceptable carrier" is any physiological carrier known to those of ordinary skill in the art useful in formulating pharmaceutical compositions.

In one preferred embodiment the pharmaceutical carrier may be a liquid and the pharmaceutical composition would be in the form of a solution. In another equally preferred embodiment, the pharmaceutically acceptable carrier is a solid and the composition is in the form of a powder or tablet. In a further embodiment, the pharmaceutical carrier is a gel and the composition is in the form of a suppository or cream. In a further embodiment the compound may be formulated as a part of a pharmaceutically acceptable transdermal patch.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellent.

Liquid pharmaceutical compositions which are sterile solutions or suspensions can be utilized by for example, intramuscular, intrathecal, epidural, intraperitoneal or subcutaneous injection. Sterile solutions can also be administered intravenously. The compounds may be prepared as a sterile solid composition which may be dissolved or suspended at the time of administration using sterile water, saline, or other appropriate sterile injectable medium. Carriers are intended to include necessary and inert binders, suspending agents, lubricants, flavorants, sweeteners, preservatives, dyes, and coatings.

The inhibitor can be administered orally in the form of a sterile solution or suspension containing other solutes or suspending agents, for example, enough saline or glucose to make the solution isotonic, bile salts, acacia, gelatin, sorbitan monoleate, polysorbate 80 (oleate esters of sorbitol and its anhydrides copolymerized with ethylene oxide) and the like.

The inhibitor can also be administered orally either in liquid or solid composition form. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

Optimal dosages to be administered may be determined by those skilled in the art, and will vary with the particular inhibitor in use, the strength of the preparation, the mode of administration, and the advancement of the disease condition or abnormality. Additional factors depending on the particular subject being treated will result in a need to adjust dosages, including subject age, weight, gender, diet, and time of administration.

This invention provides a method of treating an abnormality in a subject which is alleviated by increasing the level of a heat shock protein, which comprises administering to the subject an effective amount of an inhibitor which inhibits the cysteine protease which cleaves the same bond as the cysteine protease inhibited by N-acetyl-leucyl-leucyl-norleucinal, so as to increase the level of the heat shock protein, thereby treating the abnormality. In a preferred embodiment the heat shock protein is Heat Shock Protein 70. In a further preferred embodiment the Heat Shock Protein 70 is Heat Shock Protein 72. In a preferred embodiment the inhibitor is an aldehydic tripeptide. In a preferred embodiment the aldehydic tripeptide is N-acetyl-leucyl-leucyl-norleucinal. In another preferred embodiment the aldehydic tripeptide is N-acetyl-leucyl-leucyl-methioninal. The subject may be a mammal or a human subject. In one embodiment the abnormal condition is caused by exposure to extreme temperature changes. In another embodiment the abnormal condition caused by exposure to extreme temperature changes is frost bite. In a further embodiment the abnormal condition caused by exposure to extreme temperature changes is a burn. In one embodiment the abnormal condition is caused by a state of ischemia. In another embodiment the abnormal condition is caused by a state of hypoxia. In a further embodiment the abnormal condition is caused by anoxia. In one embodiment the abnormal condition is caused by exposure to cell toxins. In a further embodiment the cell toxin causing the abnormal condition is a heavy metal. In another embodiment the heavy metal causing the abnormal condition may be cadmium. In a further embodiment the heavy metal causing the abnormailty may be tin. In yet another embodiment the abnormal condition is caused by exposure to oxidative stress. In a still further embodiment the abnormal condition is caused by atherosclerotic lesions.

This invention provides a method of treating an abnormality in a subject which is alleviated by increasing the level of a heat shock protein, which comprises administering to the subject an effective amount of an inhibitor which inhibits a proteasome, so as to increase the level of the heat shock protein, thereby treating the abnormality. In a preferred embodiment the heat shock protein is Heat Shock Protein 70. In a further preferred embodiment the Heat Shock Protein 70 is Heat Shock Protein 72. In a preferred embodiment the inhibitor is an aldehydic tripeptide. In a further preferred embodiment the aldehydic tripeptide may be N-acetyl-leucyl-leucyl-norleucinal, N-acetyl-leucyl-leucyl-methioninal, or Cbz-leucyl-leucyl-leucinal. In a preferred embodiment the poteasome inhibitor is lactacystin. The subject may be a mammal or a human. In one embodiment the abnormal condition is caused by exposure to extreme temperature changes. In another embodiment the abnormal condition caused by exposure to extreme temperature changes is frost bite. In a further embodiment the abnormal condition caused by exposure to extreme temperature changes is a burn. In one embodiment the abnormal condition is caused by a state of ischemia. In another embodiment the abnormal condition is caused by a state of hypoxia. In a further embodiment the abnormal condition is caused by anoxia. In one embodiment the abnormal condition is caused by exposure to cell toxins. In a further embodiment the cell toxin causing the abnormal condition is a heavy metal. In another embodiment the heavy metal causing the abnormal condition may be cadmium. In a further embodiment the heavy metal causing the abnormailty may be tin. In yet another embodiment the abnormal condition is caused by exposure to oxidative stress. In a still further embodiment the abnormal condition is caused by atherosclerotic lesions.

This invention provides a method of treating an abnormality in a subject which is alleviated by increasing the binding of apoprotein B100 to a heat shock protein in the subject which comprises administering to the subject an effective amount of an inhibitor, which inhibits the cysteine protease which cleaves the same bond as the cysteine protease inhibited by N-acetyl-leucyl-leucyl-norleucinal, so as to increase the binding of apoprotein B100 to a heat shock protein, thereby treating the abnormality. In a preferred embodiment the heat shock protein is Heat Shock Protein 70. In a further preferred embodiment the Heat Shock Protein 70 is Heat Shock Protein 72. In a preferred embodiment the inhibitor is an aldehydic tripeptide. In a further preferred embodiment the aldehydic tripeptide is N-acetyl-leucyl-leucyl-norleucinal or N-acetyl-leucylleucyl-methioninal. The subject may be a mammal or a human. In one embodiment the abnormal condition is caused by exposure to extreme temperature changes. In another embodiment the abnormal condition caused by exposure to extreme temperature changes is frost bite. In a further embodiment the abnormal condition caused by exposure to extreme temperature changes is a burn. In one embodiment the abnormal condition is caused by a state of ischemia. In another embodiment the abnormal condition is caused by a state of hypoxia. In a further embodiment the abnormal condition is caused by anoxia. In one embodiment the abnormal condition is caused by exposure to cell toxins. In a further embodiment the cell toxin causing the abnormal condition is a heavy metal. In another embodiment the heavy metal causing the abnormal condition may be cadmium. In a further embodiment the heavy metal causing the abnormailty may be tin. In yet another embodiment the abnormal condition is caused by exposure to oxidative stress. In a still further embodiment the abnormal condition is caused by atherosclerotic lesions.

This invention provides a method of treating an abnormality in a subject which is alleviated by increasing the binding of apoprotein B100 to a heat shock protein in the subject which comprises administering to the subject an effective amount of an inhibitor which inhibits a proteasome, so as to increase the binding of apoprotein B100 to a heat shock protein, thereby treating the abnormality. In a preferred embodiment the heat shock protein is Heat Shock Protein 70. In a further preferred embodiment the Heat Shock Protein 70 is Heat Shock Protein 72. In a preferred embodiment the inhibitor is an aldehydic tripeptide. In a further preferred embodiment the aldehydic tripeptide may be N-acetyl-leucyl-leucyl-norleucinal, N-acetyl-leucyl-leucyl-methioninal or Cbz-leucyl-leucyl-leucinal. In a preferred embodiment the inhibitor is lactacystin. The subject may be a mammal or a human. In one embodiment the abnormal condition is caused by exposure to extreme temperature changes. In another embodiment the abnormal condition caused by exposure to extreme temperature changes is frost bite. In a further embodiment the abnormal condition caused by exposure to extreme temperature changes is a burn. In one embodiment the abnormal condition is caused by a state of ischemia. In another embodiment the abnormal condition is caused by a state of hypoxia. In a further embodiment the abnormal condition is caused by anoxia. In one embodiment the abnormal condition is caused by exposure to cell toxins. In a further embodiment the cell toxin causing the abnormal condition is a heavy metal. In another embodiment the heavy metal causing the abnormal condition may be cadmium. In a further embodiment the heavy metal causing the abnormailty may be tin. In yet another embodiment the abnormal condition is caused by exposure to oxidative stress. In a still further embodiment the abnormal condition is caused by atherosclerotic lesions.

This invention provides a method of treating an abnormality in a subject which is alleviated by selectively increasing the level of a heat shock protein, which comprises administering to the subject an effective amount of the pharmaceutical composition comprising an effective amount of an inhibitor which inhibits the cysteine protease which cleaves the same bond as the cysteine protease inhibited by N-acetyl-leucyl-leucyl-norleucinal, and a pharmaceutically acceptable carrier, thereby treating the abnormality. In a preferred embodiment the heat shock protein is Heat Shock Protein 70. In a further preferred embodiment the Heat Shock Protein 70 is Heat Shock Protein 72. In a preferred embodiment of the invention the inhibitor is an aldehydic tripeptide. In a further preferred embodiment the aldehydic tripeptide is N-acetyl-leucyl-leucyl-norleucinal or N-acetyl-leucyl-leucyl-methioninal. The subject may be a mammal or a human. In one embodiment the abnormal condition is caused by exposure to extreme temperature changes. In another embodiment the abnormal condition caused by exposure to extreme temperature changes is frost bite. In a further embodiment the abnormal condition caused by exposure to extreme temperature changes is a burn. In one embodiment the abnormal condition is caused by a state of ischemia. In another embodiment the abnormal condition is caused by a state of hypoxia. In a further embodiment the abnormal condition is caused by anoxia. In one embodiment the abnormal condition is caused by exposure to cell toxins. In a further embodiment the cell toxin causing the abnormal condition is a heavy metal. In another embodiment the heavy metal causing the abnormal condition may be cadmium. In a further embodiment the heavy metal causing the abnormailty may be tin. In yet another embodiment the abnormal condition is caused by exposure to oxidative stress. In a still further embodiment the abnormal condition is caused by atherosclerotic lesions.

This invention provides a method of treating an abnormality in a subject which is alleviated by selectively increasing the level of a heat shock protein, which comprises administering to the subject an effective amount of a pharmaceutical composition comprising an effective amount of an inhibitor which inhibits a proteasome, and a pharmaceutically acceptable carrier, thereby treating the abnormality. In a preferred embodiment the heat shock protein is Heat Shock Protein 70. In a further preferred embodiment the Heat Shock Protein 70 is Heat Shock Protein 72. In a preferred embodiment of the invention the proteasome inhibitor is an aldehydic tripeptide. In a further preferred embodiment the aldehydic tripeptide is N-acetyl-leucyl-leucyl-norleucinal, N-acetyl-leucyl-leucyl-methioninal, or Cbz-leucyl-leucyl-leucinal. In a preferred embodiment of the invention the proteasome inhibitor is lactacystin. The subject may be a mammal or a human. In one embodiment the abnormal condition is caused by exposure to extreme temperature changes. In another embodiment the abnormal condition caused by exposure to extreme temperature changes is frost bite. In a further embodiment the abnormal condition caused by exposure to extreme temperature changes is a burn. In one embodiment the abnormal condition is caused by a state of ischemia. In another embodiment the abnormal condition is caused by a state of hypoxia. In a further embodiment the abnormal condition is caused by anoxia. In one embodiment the abnormal condition is caused by exposure to cell toxins. In a further embodiment the cell toxin causing the abnormal condition is a heavy metal. In another embodiment the heavy metal causing the abnormal condition may be cadmium. In a further embodiment the heavy metal causing the abnormailty may be tin. In yet another embodiment the abnormal condition is caused by exposure to oxidative stress. In a still further embodiment the abnormal condition is caused by atherosclerotic lesions.

This invention provides a method of preserving organs ex vivo, which comprises contacting the organ with an effective amount of an inhibitor which inhibits the cysteine protease which cleaves the same bond as the cysteine protease inhibited by N-acetyl-leucyl-leucyl-norleucinal, so as to increase the level of Heat Shock Protein 70, thereby preserving the organ. In a preferred embodiment the Heat Shock Protein 70 is Heat Shock Protein 72. In a preferred embodiment of the invention the inhibitor is an aldehydic tripeptide. In a further preferred embodiment the aldehydic tripeptide is N-acetyl-leucyl-leucyl-norleucinal or N-acetyl-leucyl-leucyl-methioninal.

This invention provides a method of preserving organs ex vivo, which comprises contacting the organ with an effective amount of an inhibitor which inhibits a proteasome, so as to increase the level of Heat Shock Protein 70, thereby preserving the organ. In a preferred embodiment the Heat Shock Protein 70 is Heat Shock Protein 72. In a preferred embodiment of the invention the proteasome inhibitor is an aldehydic tripeptide. In a further preferred embodiment the aldehydic tripeptide is N-acetyl-leucyl-leucyl-norleucinal, N-acetyl-leucyl-leucyl-methioninal, or Cbz-leucyl-leucyl-leucinal. In a preferred embodiment of the invention the proteasome inhibitor is lactacystin.

This invention provides a method of preserving organs ex vivo, which comprises contacting the organ with an effective amount of a pharmaceutical composition comprising an effective amount of an inhibitor which inhibits the cysteine protease which cleaves the same bond as the cysteine protease inhibited by N-acetyl-leucyl-leucyl-norleucinal, and a pharmaceutically acceptable carrier, so as to increase the level of Heat Shock Protein 70 thereby preserving the organ. In a preferred embodiment the Heat Shock Protein 70 is Heat Shock Protein 72. In a preferred embodiment of the invention the inhibitor is an aldehydic tripeptide. In a further preferred embodiment the aldehydic tripeptide is N-acetyl-leucyl-leucyl-norleucinal or N-acetyl-leucyl-leucyl-methioninal.

This invention provides a method of preserving organs ex vivo, which comprises contacting the organ with an effective amount of a pharmaceutical composition comprising an effective amount of an inhibitor which inhibits a proteasome, and a pharmaceutically acceptable carrier, so as to increase the level of Heat Shock Protein 70 thereby preserving the organ. In a preferred embodiment the Heat Shock Protein 70 is Heat Shock Protein 72. In a preferred embodiment of the invention the proteasome inhibitor is an aldehydic tripeptide. In a further preferred embodiment the aldehydic tripeptide may be N-acetyl-leucyl-leucyl-norleucinal, N-acetyl-leucyl-leucyl-methioninal or Cbz-leucyl-leucyl-leucinal. In a preferred embodiment the proteasome inhibitor is lactacystin.

This invention provides a method of preserving organs in viva, which comprises contacting an effective amount of an inhibitor which inhibits the cysteine protease which cleaves the same bond as the cysteine protease inhibited by N-acetyl-leucyl-leucyl-norleucinal, with the organ, so as increase the level of Heat Shock Protein 70, thereby preserving the organ. In a preferred embodiment the Heat Shock Protein 70 is Heat Shock Protein 72. In a preferred embodiment of the invention the inhibitor is an aldehydic tripeptide. In a further preferred embodiment the aldehydic tripeptide is N-acetyl-leucyl-leucyl-norleucinal or N-acetyl-leucyl-leucyl-methioninal.

This invention provides a method of preserving organs in vivo, which comprises contacting an effective amount of an inhibitor which inhibits a proteasome, so as increase the level of Heat Shock Protein 70, thereby preserving the organ. In a preferred embodiment the Heat Shock Protein 70 is Heat Shock Protein 72. In a preferred embodiment of the invention the proteasome inhibitor is an aldehydic tripeptide. In a further preferred embodiment the aldehydic tripeptide is N-acetyl-leucyl-leucyl-norleucinal, N-acetyl-leucyl-leucyl-methioninal, or Cbz-leucyl-leucyl-leucinal. In a preferred embodiment of the invention the proteasome inhibitor is lactacystin.

This invention provides a method of preserving organs in vivo, which comprises contacting the organ with an effective amount of a pharmaceutical composition comprising an effective amount of an inhibitor which inhibits the cysteine protease which cleaves the same bond as the cysteine protease inhibited by N-acetyl-leucyl-leucyl-norleucinal, and a pharmaceutically acceptable carrier, so as to increase the level of Heat Shock Protein 70 thereby preserving the organ. In a preferred embodiment the Heat Shock Protein 70 is Heat Shock Protein 72. In a preferred embodiment of the invention the inhibitor is an aldehydic tripeptide. In a further preferred embodiment the aldehydic tripeptide is N-acetyl-leucyl-leucyl-norleucinal or N-acetyl-leucyl-leucyl-methioninal.

This invention provides a method of preserving organs in vivo, which comprises contacting an effective amount of a pharmaceutical composition comprising an effective amount of an inhibitor which inhibits a proteasome, and a pharmaceutically acceptable carrier with the organ, so as to increase the level of Heat Shock Protein 70, thereby preserving the organ. In a preferred embodiment the Heat Shock Protein 70 is Heat Shock Protein 72. In a preferred embodiment of the invention the proteasome inhibitor is an aldehydic tripeptide. In a further preferred embodiment the aldehydic tripeptide is N-acetyl-leucyl-leucyl-norleucinal, N-acetyl-leucyl-leucyl-methioninal, or Cbz-leucyl-leucyl-leucinal. In a preferred embodiment of the invention the proteasome inhibitor is lactacystin.

This invention provides a method of producing Heat Shock Protein 70, which comprises: (a) inserting nucleic acid encoding the Heat Shock Protein 70 into a suitable vector; (b) inserting the resulting vector into a suitable host cell, so as to obtain a cell which expresses the nucleic acid which produces the Heat Shock Protein 70 ; (c) contacting a plurality of cells from step (b) with an inhibitor which inhibits the cysteine protease which cleaves the same bond as the cysteine protease inhibited by N-acetyl-leucyl-leucyl-norleucinal; (d) recovering the Heat Shock Protein 70 produced by the cells; and (e) purifying the Heat Shock Protein 70 so recovered.

In an embodiment the heat shock protein 70 produced is Heat Shock Protein 72. In a preferred embodiment of the invention the inhibitor in step (c) is an aldehydic tripeptide. In a further preferred embodiment the aldehydic tripeptide is N-acetyl-leucyl-leucyl-norleucinal. In another preferred embodiment the aldehydic tripeptide is N-acetyl-leucyl-leucyl-methioninal.

This invention provides a method of producing Heat Shock Protein 70, which comprises: (a) inserting nucleic acid encoding the Heat Shock Protein 70 into a suitable vector; (b) inserting the resulting vector into a suitable host cell, so as to obtain a cell which expresses the nucleic acid which produces the Heat Shock Protein 70 ; (c) contacting a plurality of cells from step (b) with an inhibitor which inhibits a proteasome, so as to increase the level of Heat Shock Protein 70 ; (d) recovering the Heat Shock Protein 70 produced by the cells; and (e) purifying the Heat Shock Protein 70 so recovered.

In an embodiment the heat shock protein 70 produced is Heat Shock Protein 72. In a preferred embodiment of the invention the proteasome inhibitor in step (c) is an aldehydic tripeptide. In a further preferred embodiment the aldehydic tripeptide is N-acetyl-leucyl-leucyl-norleucinal. In another preferred embodiment the aldehydic tripeptide is N-acetyl-leucyl-leucylmethioninal. In another preferred embodiment the aldehydic tripeptide is Cbz-leucyl-leucyl-leucinal. In a preferred embodiment of the invention the proteasome inhibitor in step (c) is lactacystin.

This invention provides a method of producing the protein characterized by increased levels of the protein in a cell in response to contacting the cell with an effective amount of an inhibitor which inhibits the cysteine protease which cleaves the same bond as the cysteine protease inhibited by N-acetyl-leucyl-leucyl-norleucinal, which comprises: (a) inserting nucleic acid encoding the protein, into a suitable vector; (b) inserting the resulting vector into a suitable host cell, so as to obtain a cell which expresses the nucleic acid which produces the protein; (c) contacting a plurality of cells from step (b) with an inhibitor which inhibits the cysteine protease which cleaves the same bond as the cysteine protease inhibited by N-acetyl-leucyl-leucyl-norleucinal; (d) recovering the protein produced by the cells of step (c); and (e) purifying the protein so recovered. In a preferred embodiment of the invention the inhibitor in step (c) is an aldehydic tripeptide. In a further preferred embodiment the aldehydic tripeptide is N-acetyl-leucyl-leucyl-norleucinal. In another preferred embodiment the aldehydic tripeptide is N-acetyl-leucyl-leucyl-methioninal.

This invention provides a method of producing the protein in a charactcharacterized by increased levels of the protein in a cell in response to contacting the cell with an effective amount of a proteasome inhibitor, which comprises: (a) inserting nucleic acid encoding the protein, into a suitable vector; (b) inserting the resulting vector into a suitable host cell, so as to obtain a cell which expresses the nucleic acid which produces the protein; (c) contacting a plurality of cells from step (b) with an inhibitor which inhibits a proteasome, so as to increase the level of Heat Shock Protein 70; (d) recovering the protein produced by the cells of step (c); and (e) purifying the protein so recovered.

In a preferred embodiment of the invention the proteasome inhibitor in step (c) is an aldehydic tripeptide. In a further preferred embodiment the aldehydic tripeptide is N-acetyl-leucyl-leucyl-norleucinal. In another preferred embodiment the aldehydic tripeptide is N-acetyl-leucyl-leucyl-methioninal. In another preferred embodiment the aldehydic tripeptide is Cbz-leucyl-leucyl-leucinal. In a preferred embodiment of the invention the proteasome inhibitor in step (c) is lactacystin.

This invention will be better understood from the Experimental Details which follow. However, one skilled in the art will readily appreciate that the specific methods and results discussed are merely illustrative of the invention as described more fully in the claims which follow thereafter.

Experimental Details

ALLN, leupeptin, mouse anti-human Hsp72/73 monoclonal antibody, a secondary antibody conjugated with horseradish peroxidase (HRP) (goat anti-rabbit immunoglubin G [IgG]), and rabbit anti-rat IgG antibody were from Boehringer Mannheim Co. Anti-Human Hsp25 and anti-human Hsp60 monoclonal antibodies, ALLM, Calpain inhibitor peptide (CIP), dimethyl sulfoxide (DMSO) and dithiothreitol (DTT) were from Sigma. Human Hsp70 oligonucleotide probe was from Oncogene Science. This oligonucleotide was $^{32}p$ labeled at the 5'-end by T4 Kinase, which was from Biolabs. $^{32}p$ was from ICN Pharmaceutical Inc. L-[4,5-$^{3}$H] leucine was from Amersham Co. Anti-human Bip (immunoglobulin heavy chain binding protein, also called Grp78), anti-human Hsp27, anti-human Hsp60, and anti-human Hsp90 monoclonal antibodies were from Stress Genes. Anti-human Hsp86 and Hsp104 antibodies were from Affinity Bioreagent Inc. Nitrocellular transfer and immobilization membranes were from Schleicher & Schuell, Keene, N.H. RNA extraction kits were from Biotect, Tex. The polyclonal antibody against the human HSF1 protein was a generous gift from Dr. Carl Wu of the National Institute of Health (Rabindran, et al., 1993). Ethylene glycol bis(succunimidylsuccinate) (EGS) was from Pierce. Cbz-leucyl-leucyl-leucinal (MG132) was a gift of Dr. H. Ploegh at the Massachusetts Institute of Technology.

All the other tissue culture supplies and chemicals were obtained from supplies as previously described (Dixon, et al., 1991).

The HepG2 cell culture conditions were maintained as previously described (Dixon, et al., 1991). The cells were seeded into collagen-pre-coated dishes or six-well tissue culture plates and grown in complete medium containing minimum essential medium (MEM) with 0.1 mM nonessential amino acids, 1.0 mM sodium pyruvate, penicillin/streptomycin, and 10% fetal bovine serum. Cells were fed fresh complete medium every 3 days and maintained in a 5% $CO_2$ incubator. All experiments were performed by using exponentially growing cells at 90–95% confluency. For heat shock treatment, the dishes were sealed with Parafilm and immersed in a water bath at 42° C. for indicated durations of time. Cells were incubated with ALLN alone at indicated concentrations or combined with other chemicals at 37° C. Cells were also incubated with different protease inhibitors alone at indicated concentrations or combined with other chemicals at 37° C.

HepG2 cells were preincubated for 4 hours in serum-free MEM and then radiolabeled with $^3$H-Leucine (150 µCi/ml) in a serum-free, leucine-free medium. Preincubation and labeling media each contained either 1.5% bovine serum albumin (BSA) alone, or BSA plus ALLN (40 µg/ml except as otherwise indicated), or BSA plus other protease inhibitors at concentrations indicated in the figure legends. At the indicated times, cells were removed from the 37° C. incubator and placed on ice, washed with cold phosphate-buffer saline (PBS) twice and lysed with lysis buffer containing 1% Triton X-100 (TX100), 1% deoxycholic acid (DOC) and 0.1% SDS in PBS containing proteinase inhibitors: 2 mM phenylmethylsulfonyl fluoride (PMSF); 2 µg/ml ALLN; 2 µg/ml leupeptin; and 2 µg/ml aprotinin. After a 30 min. incubation with lysis buffer at 4° C., the lysates were centrifuged at 14,000 g in a microcentrifuge for 5 min., and the supernatants were adjusted to 1% SDS concentration and boiled for 5 min. to denature the proteins. 1% TX100 was then added to dilute the lysates to a final concentration of 0.1% SDS. Cell lysates containing equal amounts of trichloroacetic acid (TCA)-insoluble radioactivity were used for immunoprecipitations by incubating with individual monoclonal antibody (1 µg/ml) for 2.5 hours at 4° C. Protein-A Sepharose 4B was added afterwards and the lysates incubated for another 1.5 hours at 4° C. to collect the immunocomplexes. After washing four times with 1×NET buffer (containing 0.5% TX100, 0.1% SDS), the immunocomplexes were mixed with sample buffer and boiled for 5 min. Following centrifugation, the supernatants were aliquoted for scintillation counting and for 3–15% gradient polyacrymide gel electrophoresis (SDS-PAGE). The gels were later subjected to fluorography. All values are presented as the mean ± S.D. from three individual experiments except as otherwise indicated.

Total RNA was prepared using the procedure of Chomczynski and Sacchi (Chomczynski, et al., 1987) and a commercially prepared reagent, TRISOLV™ (Biotecx Laboratories Inc., Tex.). Equal amounts of tRNA samples (10 µg) were size-fractionated on a 1% agarose-formaldehyde gel according to the methods described (Maniatis, et al., 1982) and transferred to a piece of QIAGEN plus nylon membrane. To determine loading and transfer efficiency, RNA was stained with ethidium bromide before and after transfer. The membrane was baked for 30 min. at 80° C. in vacuo (a vacuum) followed by UV cross-linking. It was then incubated for 4 hours at 65° C. in a prehybridization mixture containing 10% dextran sulfate, 1% SDS, 1M sodium chloride, 50 mM Tris-HCl (pH 7.5) and 100 µg/ml denatured salmon sperm DNA. Hybridization was carried out for 18 hours at 65° C. in the same buffer with a $^{32}$P-labeled (1×10$^6$ cpm/ml) 40-mer oligonucleotide probe to the untranslated 5' region of a human hsp70 gene (Oncogene Science). This probe is specific for the inducible form of hsp70 (hsp72) and does not cross-hybridized to the constitutive form of hsp70 (hsp73), hsp-70B or hsp-70B' (Freeman, et al., 1993). The membrane was then washed four times with 2×SSC, 0.1% SDS at room temperature, one time at 65° C. for 30 min., and one time at room temperature again for 5 min., and finally rinsed with 2×SSC at room temperature. This membrane was air dried and exposed to X-ray film at −80° C. for 48 hours.

For measurement of the steady-state HSF1 protein levels, whole cell extracts were prepared by lysing the cells directly with 2×SDS-sample buffer (Maniatis, et al., 1982). For chemical cross-linking experiments, whole-cell extracts were prepared as described (Mosser, et al., 1988). Briefly, the cold PBS-washed cell pellets were quickly and repeatedly frozen in liquid nitrogen. The pulverized pellet material was thawed and resuspended in about 2 packed cell volumes of buffer C (20 mM N-2-hydroxyethylpiperazine-N-2-ethanesulfonic acid [HEPES; pH 7.9], 0.42 M NaCl, 1.5 mM $MgCl_2$, 0.2 mM EDTA, 0.5 mM DTT, 0.5 mM PMSF, 10 µg/ml leupeptin 10 µg/ml al pepstatin, 0.01 units/ml aprotinin, 25% glycerol [v/v]). The concentration of NaCl was then adjusted to 0.38 M. After 10 min. of incubation on ice, the extract was clarified by centrifugation at 4° C. for 15 min. at 10,000×g. Cross-linking of HSF was immediately performed (Abdella, et al., 1979) by adding 1/10 volume of freshly prepared DMSO containing an appropriate concentration of EGS to the whole cell extracts of a final concentration of 1 mM and then incubating the mixture at 22° C. for 30 min. Reactions were quenched by addition of glycine to 75 mM and incubation for 15 min. at room temperature. After SDS-PAGE, the proteins were transfered to nitrocelluose, and nonspecific protein binding sites were blocked with 5% non-fat dry milk. The membrane was probed with 1:1000 dilution of anti-HSF1 antibody followed by repeated washing and subsequent incubation with the secondary antibody (horseradish peroxidase-conjugated anti-rabbit IgG) for detection of antigen-antibody complex.

Results

Figure 1B:
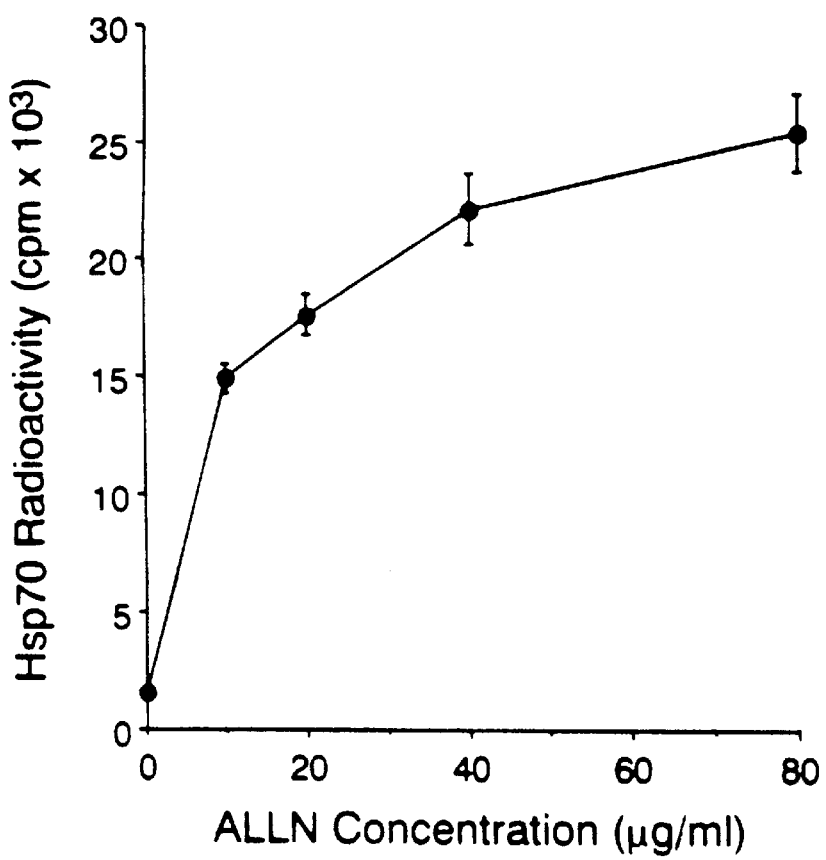
Figure 1C:
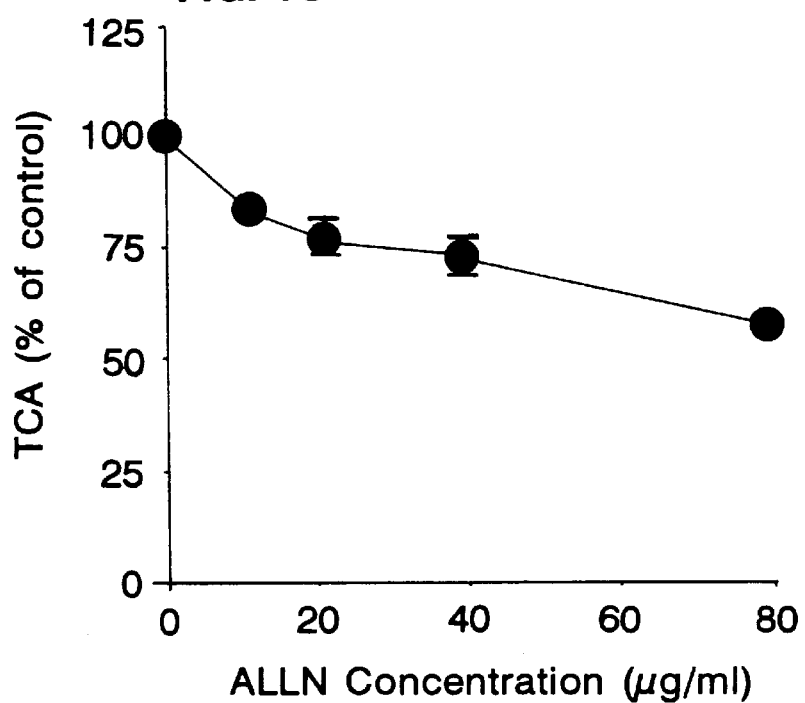

ALLN induces Hsp70 protein levels in HepG2 cells in a dose-dependent manner. The effect of ALLN on the protein levels of Hsp70 was analysed by denaturing immunoprecipitation of extracts of [$^3$H]-leucine radiolabeled HepG2 cells which had been pre-treated with ALLN for 4 hours at different doses. Denaturing immunoprecipitation was chosen because Hsp70 is a major cytosolic chaperone protein and it is co-immunoprecipitated with a number of other proteins under non-denaturing conditions (Beckmann, et al., 1990; Zhou, et al., 1995). Immunoprecipitation with anti-human Hsp70 antibody showed that untreated cells had low levels of Hsp70 (FIGS. 1A–C). This may be due to a low constitutive level of expression of Hsp73 (Hsp70) in HepG2 cells similar to that reported for other cell types in the absence of stress (Welch, et al., 1984). Treatment with ALLN was associated with a marked increase in Hsp70 level, which was further confirmed as Hsp72 (the inducible form) by Western blot (data not shown). The cellular Hsp70 levels showed a dose-dependent response to ALLN treatment. This induction effect was not related to ALLN-induced cell toxicity, since at a low concentration of ALLN (10 µg/ml), Hsp70 levels were induced more than 9-fold, while cell total incorporation of radiolabel (TCA cpm, an indicator of cell toxicity) did not change significantly (FIG. 1C, inset). When the ALLN-containing medium was removed after a 4-hour preincubation, then the cells were washed with fresh medium for different periods of time, followed by radiolabeling and immunoprecipitation of cell lysates, it was found that Hsp70 levels remained as high as 25-fold at the end of a 2-hour wash, 8-fold at the end of a 6-hour wash, and 4-fold at the end of an 8-hour wash (data not shown). Similar results were obtained from human microvascular endothelial cell line, which showed a 35-fold increment of Hsp70 level, with no change in TCA-cpm measurement after 4 hours of ALLN treatment (40 $\mu$g/ml) and 30 min. of labeling with [$^3$H]-leucine in the presence of ALLN (data not shown). In addition, it was found that Chinese hamster ovary (CHO) cells also respond to ALLN by increasing cellular Hsp70 levels (data not shown).

Figure 2A:
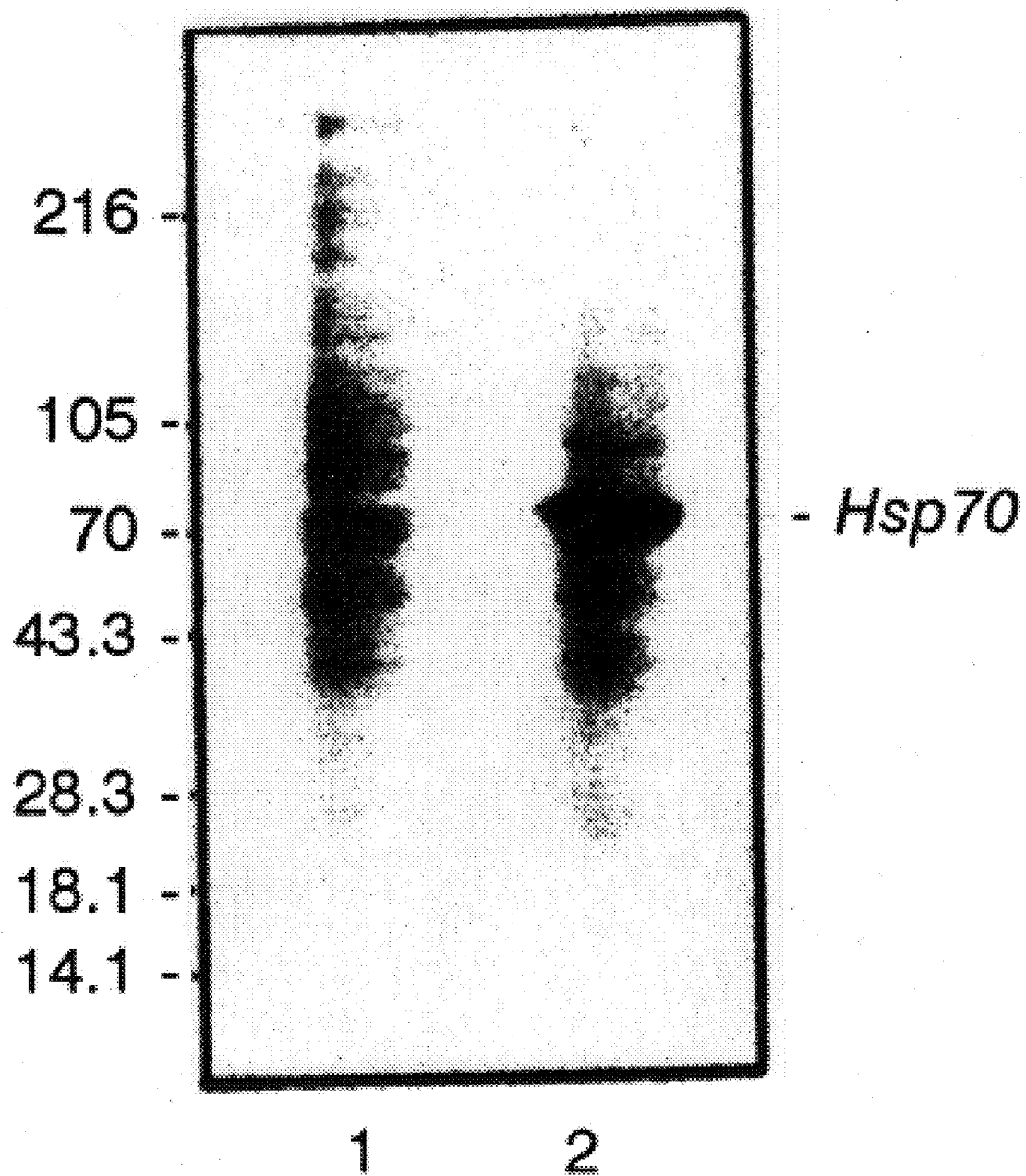
FIGS. 2A–2B: Effects of ALLN on Hsp25, Hsp60, Hsp90 and Bip biosynthesis. HepG2 cells were pre-treated and radiolabeled with/without ALLN for 4 hours as described in FIG. 1. Cell lysates were denatured and aliquoted for immunoprecipitation with anti-Hsp25, anti-Hsp60, anti-Hsp90, or anti-Bip antibodies respectively (1 $\mu$g/ml) . Because the anti-Hsp90 antibody is of rat source, rabbit anti-rat IgG antibody was added after the first incubation and the incubation was extended for another 1 hour at 4° C. before collection with protein A-Sepharose. Immunoprecipitates were aliquoted for scintillation counting and plotted. Each value is presented as means ± SD from three individual experiments.
Figure 2B:
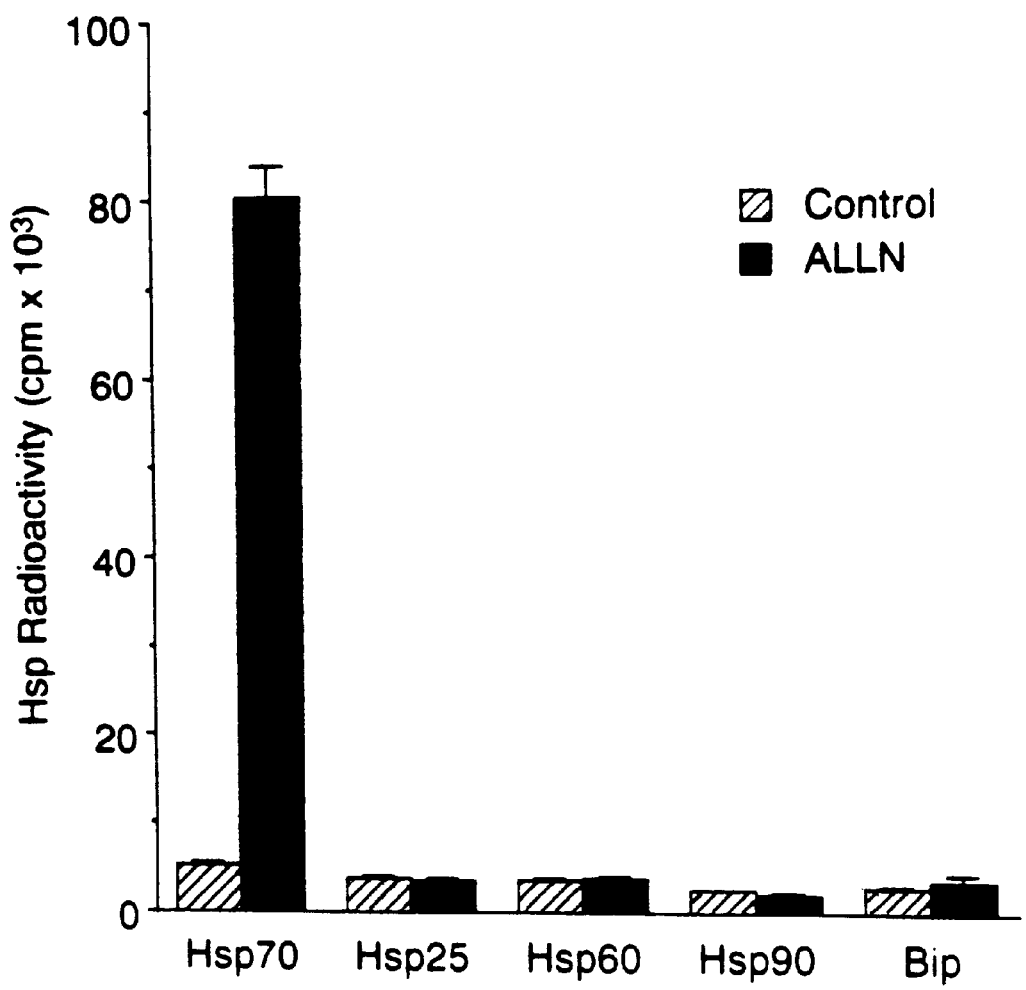
Figure 7B:
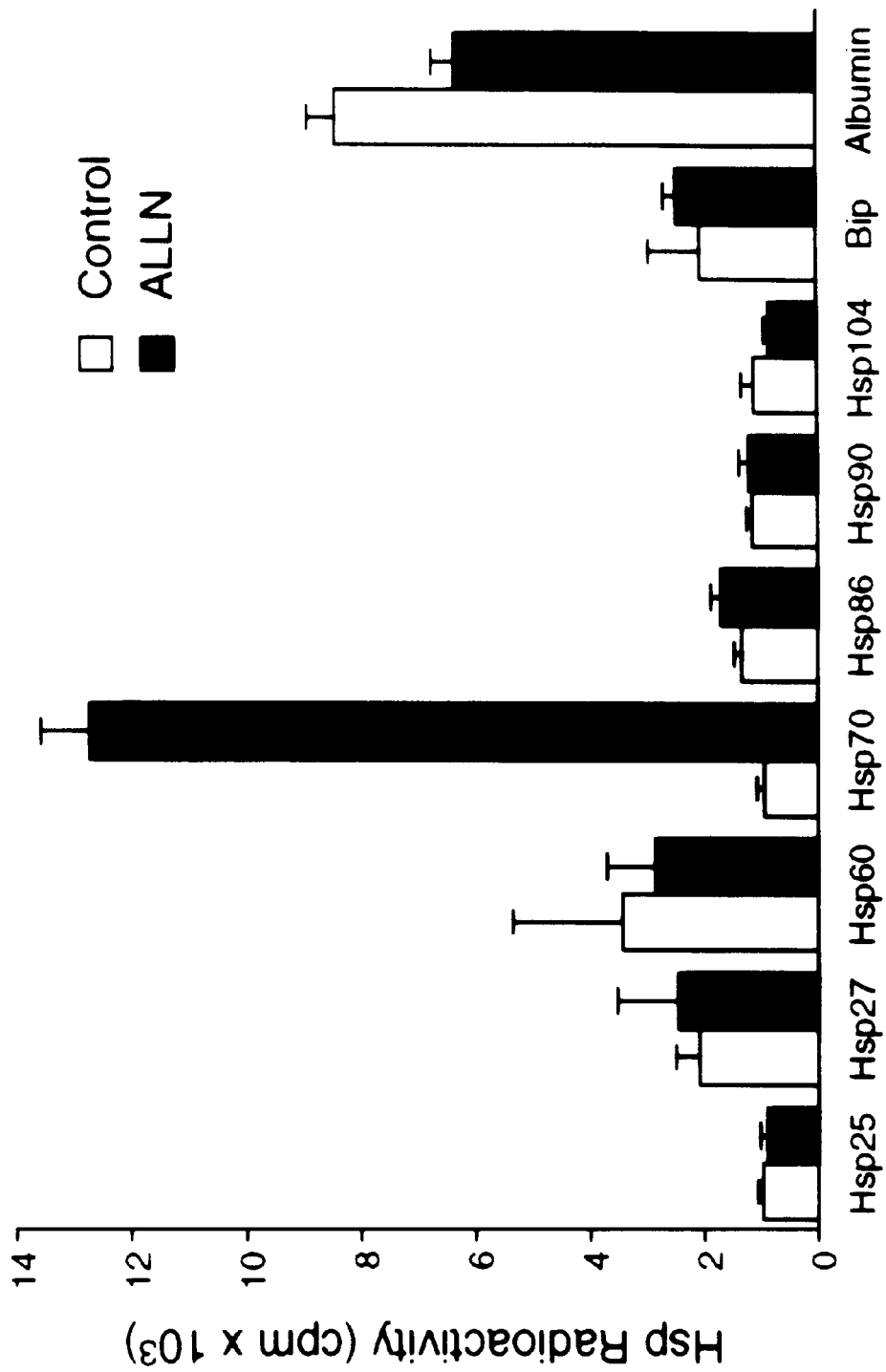

Hsp70 was found to be selectively induced by ALLN. It was reported (Liu, et al., 1989) that in human diploid fibroblasts, heat shock treatment could induce the synthesis of several members of the Hsp family, including Hsp25, Hsp50, Hsp64, Hsp72, Hsp78, Hsp89 and Hsp98. Short, sublethal episodes of cardiac ischemia increase both Hsp70 and Hsp60 (Marber, et al., 1988). Such complex induction patterns may reflect an increased requirement for several of these Hsps, i.e., the need for several of these Hsps to increase, in order to prevent or protect pre-existing proteins from denaturation. Many investigators have suggested that molecular chaperones like Hsp70 and Hsp60 may work in tandem to faciliate the folding process (Hartl and Martin, 1992). To ascertain whether other members of the Hsp family are also induced by ALLN treatment, the whole-cell protein pattern of untreated and ALLN-treated HepG2 cells was compared by directly loading the [$^3$H]-leucine-labeled cell lysates onto SDS-PAGE gel. As can been seen in FIG. 2A, all the proteins were synthesized at similar levels in both ALLN-treated and control cells, except for Hsp70, which was markedly increased, and a protein of about 80–90 kDa, which was also increased but not as significantly as Hsp70. As can been seen in FIG. 7A, all the proteins were synthesized at similar levels in both ALLN-treated and control cells, except for Hsp70, which was markedly increased in ALLN-treated cells. To further confirm this result, the protein levels of Hsp90, Hsp60, Hsp25, Hsp27, Hsp86, Hsp104, Bip and albumin were selectively determined by specific immunoprecipitation of each protein with corresponding antibody from radiolabeled extracts of cells incubated with or without ALLN. As can be seen in FIG. 2B and in FIG. 7B, only Hsp70 was induced by ALLN treatment in HepG2 cells. This result indicates that the ALLN-induced 80–90 kDa protein observed in FIG. 2A is not Hsp90. It would be interesting to characterize this polypeptide and to identify its roles in the ALLN-induced cellular response.

Figure 3A:
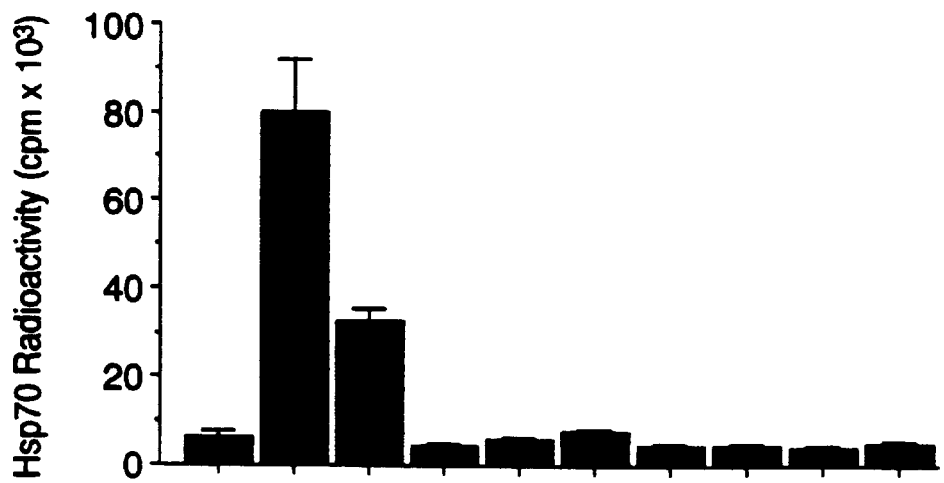
FIGS. 3A–3B: Effects of the other protease inhibitors on Hsp70 biosynthesis in HepG2 cells. HepG2 cells were preincubated in serum-free MEM containing either 1.5% BSA alone (Control), or BSA plus 40 $\mu$g/ml of ALLN, 40 $\mu$g/ml of ALLM, 50 $\mu$g/ml of leupeptin, 50 $\mu$g/ml of pepstatin A, 25 $\mu$g/ml of E-64d, 1 mM of phenylmethylsulfonyl fluoride (PMSF) , 100 KIU/ml of apotinin, 1 mM of Benzamidine (Benz), 200$\mu$M of calpain inhibitor peptide (CIP). Radiolabeling (in the presence of protease inhibitors), lysis and immunoprecipitation were performed as described in FIG. 1. The Hsp70 specific radioactivity (A) and the amount of total incorporated radioactivity (TCA-cpm) (B) were compared with each other. All the values were presented as the mean ± SD from three individual culture dishes.
Figure 3B:
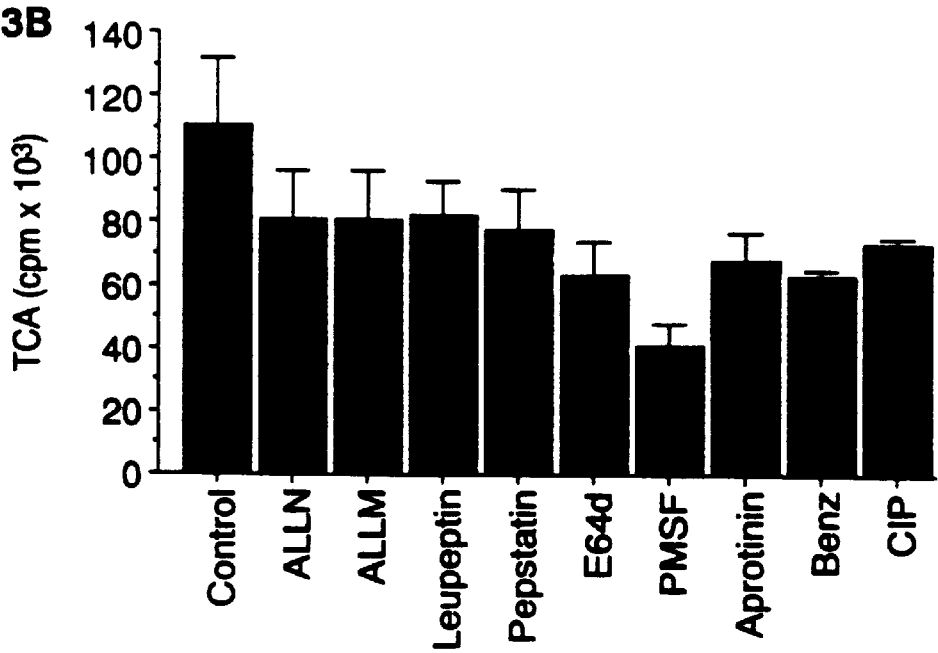

Hsp70 was induced by ALLN other proteasome inhibitors, and, less potently, by ALLM, but not by other proteinase inhibitors tested. ALLN is a synthetic aldehydic tripeptide which can, in vitro, inhibit the activity of $Ca^{2+}$-dependent neutral cysteine proteases. Recently, ALLN has been shown to inhibit proteasome activity (Rock, et al., 1994; Ward, et al., 1995; Lowe, et al. 1995). ALLN can also inhibit lysosomal proteases, including cathepsin L, cathepsin B and calpain D (Hiwasa, et al., 1990). The effects of several other protease inhibitors on Hsp70 were examined. Cells were pre-treated with various protease inhibitors for 4 hours prior to radiolabeling, cell lysis and immunoprecipitation (FIG. 3). Total incorporation of radiolabeled leucine into proteins (TCA cpm) was measured as an indicator of both cell toxicity and entrance of the drugs into the cells.

Although all the tested protease inhibitors, at the given concentrations, showed similar degree of cell toxicity (FIG. 3, B), only ALLN and ALLM, among the 9 different protease inhbitors tested, were able to significantly induce Hsp70 (FIG. 3, A) . ALLM, which is almost identical to ALLN in its structure, showed less ability to induce Hsp70 levels. E-64d (N[N-L-trans-carboxyoxiran-2-carbonyl-L-leucyl]-agmatine), which like ALLN, is considered to be a specific inhibitor of cysteine proteases, showed a very weak effect on Hsp70. Leupeptin, an inhibitor of both serine and cysteine proteases, was ineffective. No induction of Hsp70 was observed with two other serine protease inhibitors, aprotinin and PMSF, nor with pepstatin, a metalloprotease inhibitor. It is of interest to note that the effect or lack of effect of these inhibitors on Hsp70 is consistent with their effects on apoB and on the enzyme 3-hydroxy-3-methylglutaryl-coenzyme A (HMG-CoA) reductase. Both of these proteins are protected by ALLN, and less effectively, by ALLM, but not by the other protease inhibitors mentioned above. (Inoue, et al.; 1991, Sakata, et al., 1993, our unpublished data).

Figure 9A:
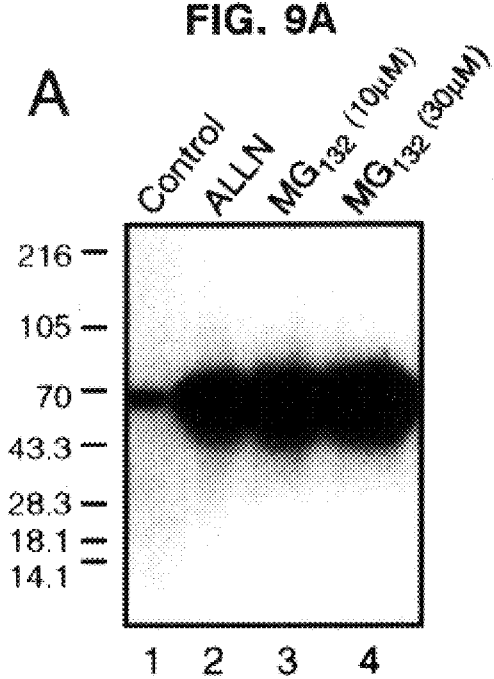
FIGS. 9A–9B: Effects of proteasome inhibitors on Hsp70 induction. HepG2 cells were preincubated with the proteasome inhibitors MG132 at a final concentration of either 10 µM or 30µM (A), or lactacystin at 10 µM (B) for 4 hours under conditions described in FIG. 3. These cells were then subjected to radiolabeling (30 min), cell lysis, and immunoprecipitation with anti-Hsp70 antibody. The experiments with MG132 (A) were repeated twice; the effects of lactacystin (B) were studied in triplicate culture dishes.
Figure 9B:
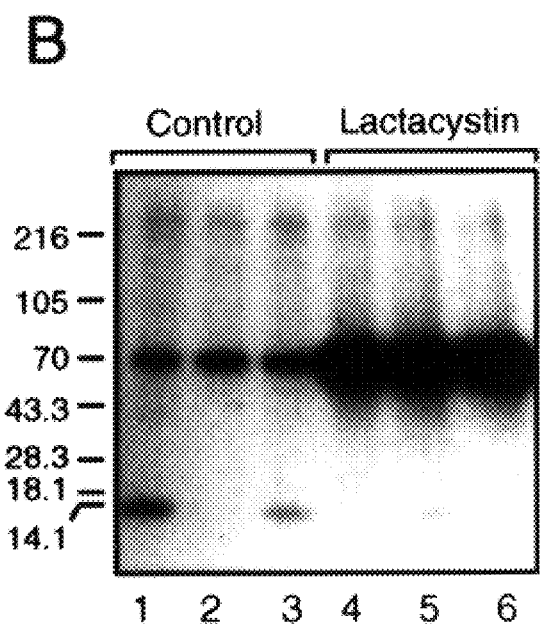

Because ALLN and ALLM are both aldehydic tripeptides, a class of compounds found to inhibit proteasomes in several recent studies (Rock, et al., 1994; Ward, et al., 1995; Lowe, et al.,1995), the effects of MG132, an aldehydic tripeptidyl proteasome inhibitor that reversibly binds to the active sites of the proteasome (Rock, et al., 1994; Goldberg, et al, 1995), and lactacystin, a structurally unique proteasome inhibitor that irreversibly acylates the active site threonine (Fenteany, et al., 1995) were determined. Both molecules induced Hsp70 levels dramatically in HepG2 cells (FIG. 9, A and B) without obvious toxicity to the cells (as indicated by TCA-precipitable radioactivities, data not shown).

Figure 8B:
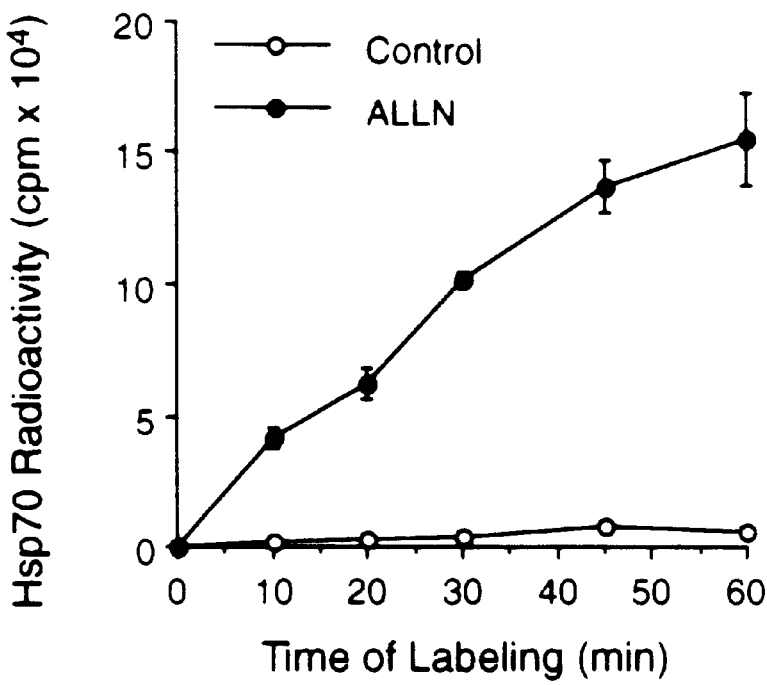

ALLN not only stabilizes Hsp70 but also increases its synthesis. To test whether ALLN induces Hsp70 by increasing protein synthesis, HepG2 cells were preincubated with or without ALLN for 4 hours at 37° C. and subsequently radiolabeled with [$^3$H]-leucine for periods between 10 and 60 min. Anti-Hsp70 immunoprecipitates were collected from cell lysates, proteins separated by SDS-PAGE (FIG. 8A), and radioactivity determined by scintillation counting (FIG. 8B). As indicated, the rate of incorporation of [$^3$H]-leucine into Hsp70 was increased about 25-fold at every time point in this experiment.

Figure 8C:
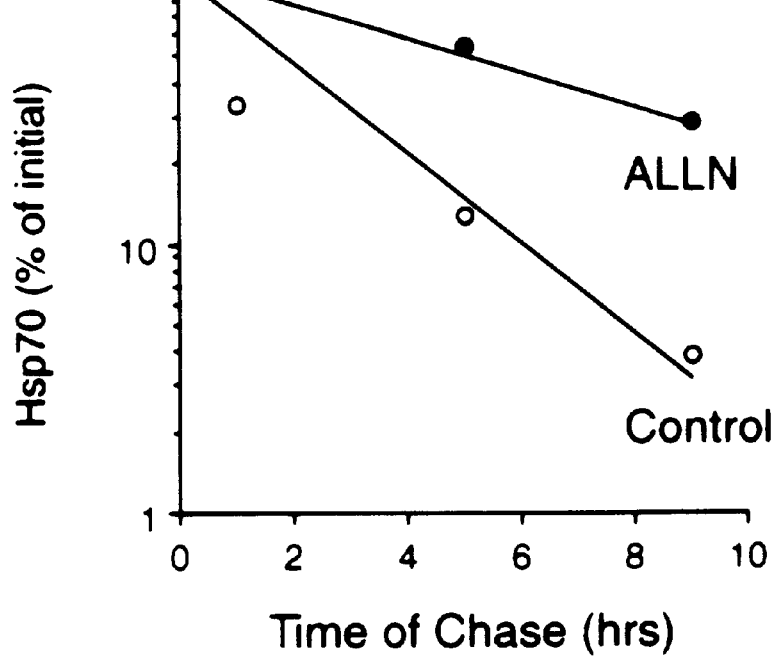

Since ALLN is a cysteine protease inhibitor, the possibility that protection of Hsp70 from proteolytic degradation accounted for the sharp increase in Hsp70 induced by ALLN was tested (Rock, et al., 1994; Ward, et al., 1995; Hiwasa, et al., 1990; Inoue, et al., 1991; and Sakata, et al., 1993). To determine whether ALLN stabilizes Hsp70, the turnover rate of radiolabeled Hsp70 in the presence or absence of ALLN (40 $\mu$g/ml) was measured in a pulse-chase experiment. FIG. 4A shows that without ALLN, newly synthesized Hsp70 disappeared rapidly, with a half life of about 2.5 hours. FIG. 8C shows that without ALLN, newly synthesized Hsp70 disappeared rapidly, with a half life of about 2 hours. This value is comparable to that reported by Landry et al. (Landry, et al., 1991) who showed that Hsp70 in Chinese hamster ovary (CHO) cells displayed a half life of about 3–4 hours. In the presence of ALLN, Hsp70 disappeared much more slowly, with a half life of about 6 hours. Thus, stabilization of Hsp70 by ALLN did contribute to the increased cellular level of this protein. However, since the 30 min. labeling of cells treated with ALLN resulted in an approximate 30-fold increment of newly synthesized Hsp70 levels (data from several experiments) compared with untreated cells, it seemed clear that a 3–4-fold increase in the half-life of Hsp70 by ALLN could not totally account for the dramatic induction of Hsp70 observed. Therefore, the dramatic Hsp70 induction by ALLN must have resulted mainly from increased protein synthesis. This was confirmed in the next study in which HepG2 cells were preincubated either with or without ALLN for 4 hours and subsequently radiolabeled with 3H-leucine for periods of time between 10–60 min. Immunoprecipitates were collected from cell lysates, proteins separated by SDS-PAGE, and radioactivity determined by scintillation counting. As expected, the rate of incorporation of 3H-leucine into Hsp70 was increased about 25-fold at every time point in this experiment (FIG. 4B).

ALLN upregulates Hsp70 transcription in a time-dependent manner and requires de novo protein synthesis. Total RNA was isolated from HepG2 cells which had been incubated for 4 hours at 37° C. (FIG. 5A) with MEM containing BSA alone (Control, lane1), BSA plus 40 $\mu$g/ml of ALLN (ALLN, lane2), BSA plus ALLN and 10 $\mu$ml of actinomycin D (A+AD, lane3) or BSA plus ALLN and 50 $\mu$g/ml of cycloheximide (A+CXM, lane4). A radioprobe containing a unique sequence specific for the 5' untranslated region of hsp72 (inducible form) (Freeman et al., 1993) was used for Northern blot analysis. This probe does not recognize hsp73 (constitutive form). Northern blotting analysis indicated that the amount of hsp70, i.e. hsp72, mRNA was increased dramatically in the ALLN-treated cells. Co-treatment of ALLN with actinomycin D, which completely blocks RNA synthesis, abolished the effects of ALLN, indicating that ALLN induced hsp70, i.e. hsp72, mRNA by increasing its synthesis rather than protecting it from degradation. It has been reported previously that induction of Hsp70 at the transcriptional level by heat shock, inorganic metals, or metalloporphyrins occurs independently of new protein synthesis (Schlesinger, et al., 1982; Mosser, et al., 1988; Zafarullah, et al., 1993; Mitani., et al; 1993), whereas induction by amino acid analogs requires ongoing protein synthesis (Mosser, et al., 1988). Therefore, the effects of the protein synthesis inhibitor cycloheximide at a level (50 $\mu$g/ml) which was sufficient to block new synthesis were examined (Baler et al.,1992). As can be seen, the marked increase in hsp70, i.e. hsp72, mRNA associated with ALLN treatment was abolished by co-treatment with cycloheximide.

Figure 5A:
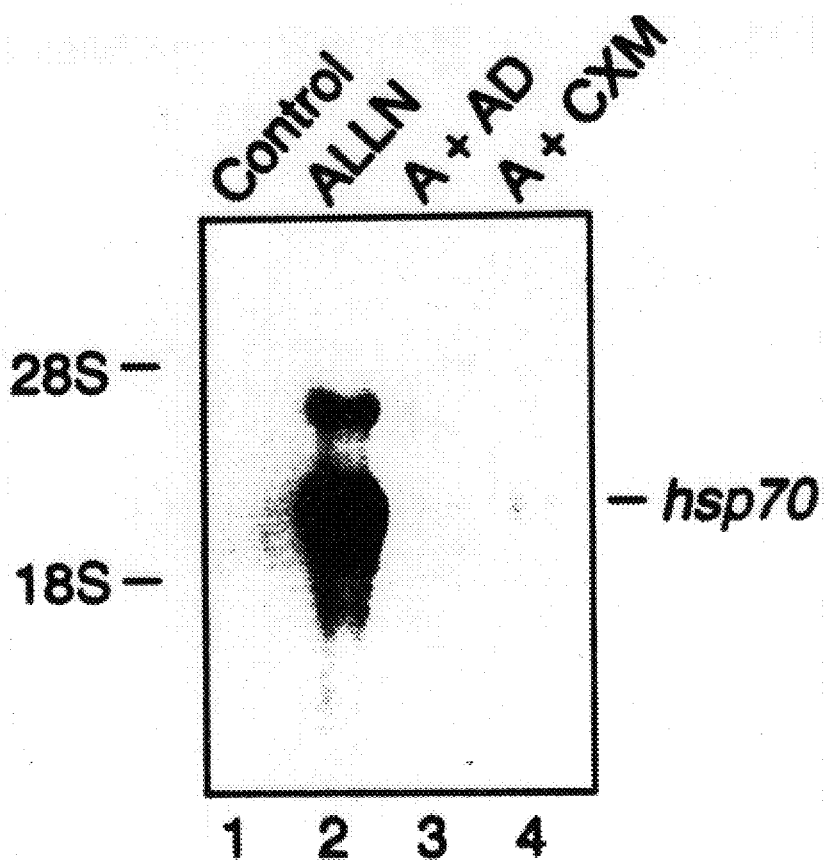
FIGS. 5A–5B: ALLN affects hsp70 gene transcription. (A). HepG2 cells were treated with serum-free MEM containing either 1.5% BSA alone (Control, lane1), BSA plus 40 µg/ml of ALLN (ALLN, lane2), ALLN and 10 µg/ml of actinomycin D (A+AD, lane3), or ALLN and 50 µg/ml of cycloheximide (A+CXM, lane4). After 4 hours treatment at 37° C., cells were harvested. (B). HepG2 cells were treated with 40 µg/ml of ALLN in the serum-free MEM for up to 0 hour (lane1), 1 hour (lane2), 2 hours (lane3), and 3 hours (lane4) and then harvested without recovery. Or after treatment for 3 hours in the presence of ALLN as above, the ALLN containing medium were removed, cells were washed and fed fresh medium containing only BSA for recovery of up to 1 hour (lane5), 3 hours (lane6), 5 hours (lane7) or 7 hours (lane8). The total RNA was prepared, and equal amounts of the samples were loaded and run on a 1% formaldehyde-agarose gel, blotted onto a nylon membrane, and subsequently hybridized with specific synthetic oligonucleotide probes for hsp70 mRNA as described under Experimental Details. The position of 28S and 18S rRNA are shown for reference. The equality of the amount of RNA loaded in each lane and the efficiency of transfer from gel to the membrane were demonstrated by staining the gels with ethidium bromide (data not shown).
Figure 5B:
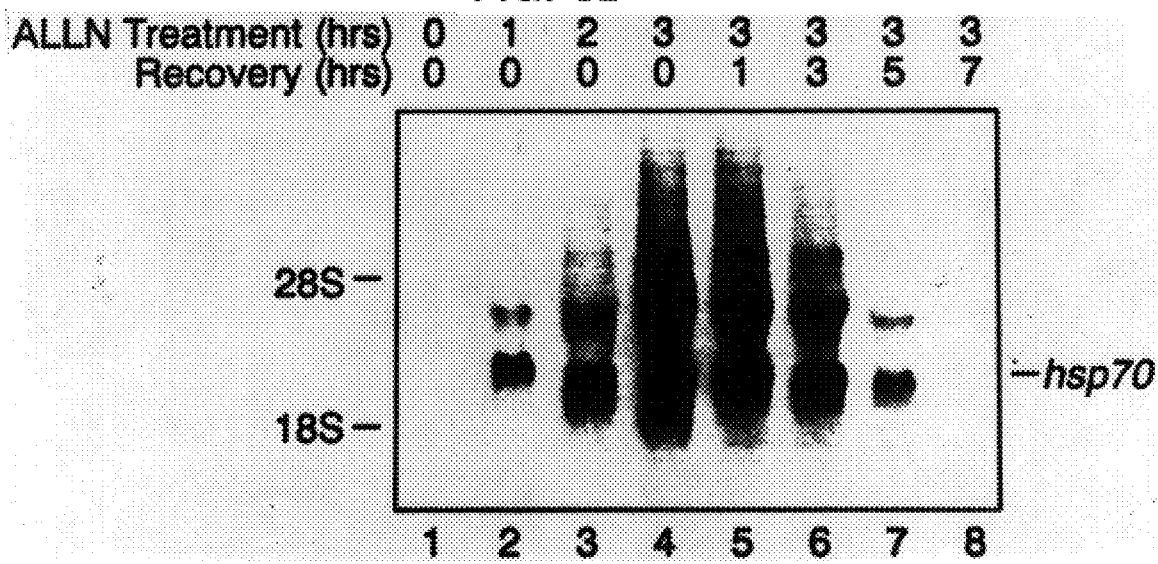

As can be seen in FIG. 5B, induction of hsp70, i.e. hsp72, mRNA by ALLN was time-dependent. Although 60 min. of ALLN treatment was already associated with a significant increase of hsp70, i.e. hsp72, mRNA levels, treatment with ALLN for 1, 2, or 3 hours increased hsp70, i.e. hsp72, mRNA in proportion to the duration of treatment (FIG. 5B, lanes1–4). After treatment for 3 hours, ALLN containing medium was removed and the cells were washed and fed fresh medium containing only BSA. As can be seen from lanes5–8, hsp70, i.e. hsp72, mRNA levels decreased progressively during recovery. After 7 hours of recovery, hsp70, i.e. hsp72, mRNA had declined to background levels (lane8). This result suggested that transcriptional induction of hsp70, i.e. hsp72, mRNA by ALLN was contingent upon the presence of ALLN and the induction was fully and rapidly reversed upon remove of ALLN.

ALLN induces trimerization of HSF1 without affecting its protein levels; trimerization is dependent on de novo protein synthesis. It is known that the heat shock transcriptional response is mediated by the activation of a pre-existing 90-kDa protein factor, heat shock factor 1, (HSF1), which binds to heat shock elements (HSE) in the promoters of heat shock genes (Sarge, et al., 1993; Baler, et al., 1993). HSF1 binding to the HSE results in a high level of transcription of hsp70, i.e. hsp72, genes. It was reported that HSF1 is the primary component of HSF-DNA activity present in cells exposed to heat shock, cadmium sulfate, and the amino acid analog, L-azetidine-2-carboxylic acid (Sarge, et al., 1993). This activation process is achieved by conversion of a latent, non-DNA-binding monomeric form of HSF1 to a DNA-binding trimer (Westwood and Wu, 1993). Western blotting techniques were used to determine the effects of ALLN treatment on the steady-state level and stoichiometry of HSF1. FIG. 6A demonstrates that the steady-state levels of HSF1 in whole cell extracts were not significantly affected either by heat shock treatment with or without cycloheximide (lanes4 and 5), or by ALLN treatment with or without cyclohexmide (lanes2 and 3), which is consistent with the reported data that HSF1 is quite stable and is regulated posttranslationally. The electrophoretic mobility of HSF1 under each condition, however, was not identical. This may represent different phosphorylation status of HSF1 under different situations (Sarge, et al, 1993; Rabindran, et al., 1994). To determine whether HSF1 undergoes a change in size upon treatment with ALLN in vivo, chemical cross-linking of subunit proteins were performed with EGS dissolved in DMSO prior to Western blot analysis of HSF1. This technique allowed for assessment of the stoichiometry of the transcriptional factor under different experimental conditions (Sarge, et al., 1993). Using this protocol, it was shown (FIG. 6B) that under control conditions, most HSF1 is in the monomer state (lane1); ALLN treatment produced a 270-kDa cross-linked product, suggesting that HSF1 in ALLN-treated cells exists as a trimer in solution (lane2). This result is comparable to the activation obtained by heat shock (lane4). Co-treatment with cyclohexmide, however, abolished the effect of ALLN on HSF1 trimerization (lane3). Cycloheximide did not, however, affect the heat shock-associated trimerization (lane5). Combining the results of FIGS. 4A and 4B, it appears that ALLN activated HSF1 without affecting its steady-state protein levels; in the presence of cyclohexmide, however, ALLN treatment was not associated with HSF1 activation to the DNA-binding, trimeric form. These results indicate that the initiation of HSF1 trimerization by ALLN requires de novo protein synthesis, which is consistent with results in an early transcriptional study (FIG. 5A). In contrast, initiation of HSF1 activation by heat shock does not require de novo protein synthesis, which is consistent with the published data from other laboratories (Mosser, et al., 1988; Goodson, et al., 1995)

Discussion

In this study, it was demonstrated that ALLN rapidly and selectively induces Hsp70 in HepG2 cells. This effect occurs in a dose- and time-dependent manner and is not related to cell toxicity. In HepG2 cells ALLN has no effects on Hsp90, Hsp60, Hsp25, Hsp27, Hsp86, Hsp104, Bip or albumin. Of the several protease inhibitors tested, only a closely related cysteine protease inhibitor, ALLM, had this effect. ALLN induces Hsp70 not only through stabilizing this protein but mainly by significantly increasing its synthesis. The ALLN-induced increase in Hsp70 synthesis resulted from increased transcription of the hsp70, i.e. hsp72, gene via activation of HSF1; the initiation of this process requires de novo protein synthesis. Finally, results of experiments with MG132 and with lactacystin, the most specific proteasome inhibitor so far reported, indicated involvement of proteasomes in the regulation of Hsp70 levels in HepG2 cells.

The actual mechanism by which the cell recognizes and responds to a particular stress is still unclear. One common denominator shared by many different agents that induce the stress response is an ability to promote, at least in vitro, the production of unfolded or abnormal proteins (Pelham, 1986). These misfolded proteins may generate signals that activate HSF1. An autoregulatory loop model has been proposed by Morimoto, et al. and several other investigators to explain the regulation of HSF1 DNA-binding activity by Hsp70 itself (Morimoto, et al; 1994; Baler, et al., 1992). According to this model, HSF1 is maintained in a non-DNA binding form through transient interaction with Hsp70 under non-stressed conditions, possibly by influencing or stabilizing a specific conformation of HSF1 void of DNA-binding activity. During heat shock, the appearance of misfolded or aggregated proteins creates a large pool of new protein substrates that compete with HSF1 for association with Hsp70, thereby removing the negative regulatory influence of Hsp70 on HSF1 DNA-binding activity. HSF1 then oligomerizes, binds DNA, and acquires transcriptional activity. The result is increased synthesis and accumulation of heat shock proteins, particularly Hsp70. When the pool of free or unassociated Hsp70 increases, as would occur during recovery from heat shock, the HSF1-Hsp70 complex reforms, attenuating the heat shock response. Although several studies support a role for Hsp70 in the autoregulation of HSF trimerization and activation, other studies have failed to observe effects of Hsp70 on either the temperature set point or magnitude of HSF activation (Rabindran, et al., 1994). On the other hand, there is substantial evidence that on-going protein synthesis is required for HSF activation and Hsp70 induction in cells treated with amino acid analogs, herbimycin A or iodoacetamide (Mosser, et al., 1988; Hedge, et al., 1995; Liu, et al., 1996). Protein synthesis does not appear to be required for the hsp70 response to either heat shock or metal ions (Mosser, et al., 1988; Goodson, et al., 1995). These observations raise the possibility that multiple pathways are available, depending on the environmental or chemical perturbation, for stress-induced hsp72 gene activation.

ALLN has been characterized by several groups as a cysteine proteinase inhibitor. (Hiwasa, et al., 1990, Inoue, et al., 1991; Sakate, et al., 1993; Sherwood, et al., 1993; Wang et al., 1994). It is logical to propose, therefore, that ALLN treatment might increase the intracellular load of denatured and/or unfolded proteins, thereby increasing the demand for Hsp70. Thus, depletion of the free Hsp70 pool might be the mechanism whereby ALLN induces Hsp70, similar to that for heat shock. Similarity between the action of ALLN and heat shock is supported by this data that (1) ALLN activates through trimerization of HSF, upregulation of hsp70 transcription, and an increase in Hsp70 synthesis; (2) induction of Hsp70 by ALLN occurs in a time- and dose-dependent manner; and (3) attenuation of the elevated transcription of hsp70 gene occurs rapidly during a recovery period.

On the other hand, these results raise the possibility that the stimulus upstream to HSF1 by which ALLN induces Hsp70 is not identical to that of heat shock. This consideration is prompted by the experiments demonstrating that co-treatment with cycloheximide blocked the ALLN-associated activation of HSF1 and concomitant increase in hsp70 gene transcription. This suggests that de novo protein synthesis is required for ALLN to induce Hsp70. In contrast, co-treatment with cycloheximide showed no effect on heat shock-induced HSF1 activation (FIG. 6B), consistent with the report by Mosser, et al. that the presence of cycloheximide affected neither heat shock-induced hsp70 transcription nor HSF1 DNA-binding activity (Mosser, et al., 1988). This discrepancy between ALLN and heat shock suggests that a newly synthesized protein factor, upstream of HSF1, regulates ALLN-induced but not heat shock-induced hsp70 gene expression. Thus, this newly synthesized protein is involved, directly or indirectly, in HSF1 trimerization. Under normal situations, this protein turns over rapidly and is degraded by a cysteine protease which is sensitive to ALLN and ALLM but resistant to other mentioned protease inhibitors. ALLN inhibits this cysteine protease and thus accumulates the rapidly-turning-over protein factor, leading to an increase in trimerization of HSF and Hsp70 synthesis. At present it is not known if the ALLN-induced 80–90 kDa protein in FIG. 2A is related to this protein factor, nor is it known if this specific pathway can account for the strict selectivity of ALLN to induce Hsp70 but not other Hsps such as Hsp25, Hsp60, Hsp90 or Bip. Further analysis of ALLN-induced HSF trimerization and the induced protein factor may provide new insights into how stress regulates gene expression.

The discovery that ALLN is a potent inducer of Hsp70 is of interest for a number of reasons. First, ALLN may be representative of a new class of signaling molecules that can influence the heat shock response. Second, the observations presented here imply that events occurring downstream of an ALLN-sensitive protease may be critical for the heat shock response. Third, the results raise the possibility that other ALLN-associated cellular phenomena, such as disruption of cell cycle (Sherwood, et is al., 1993), decreased cellular cholesterol ester formation, and inhibition of the degradation of proteins such as apoB (Sakata, et al., 1993) and HMG-CoA reductase (Inoue, et al., 1991) may be related to ALLN-induced elevations of Hsp70 levels. Finally, ALLN may have the potential for use as a pharmacological inducer of Hsp70 in both basic science laboratories and the clinical arena.

Increasing numbers of reports have shown the protective effects of Hsp70 on tissue/organs in clinically relevant situations. As a result, investigators have begun to search for efficient pharmacological means of rapidly and selectively inducing Hsp70 (in minutes or hours) (Minowada and Welch, 1995). Currently, hyperthermic treatment is the commonly used approach to induce Hsps. However, heat shock treatment is somewhat impractical particularly for homeotherms. One of the limits of this approach is that the full induction of Hsp70 by heat stress occurs 8 and 18 hours after initiation of heat treatment. Another limit is that the response to heat treatment is a whole-body rather than local response as is needed in some clinical cases. Still another disadvantage is that heat shock treatment induces several Hsps rather than Hsp70 alone. Finally, systemic heat shock is likely to have some adverse effects that reduce its attractiveness as a treatment modality. These studies suggest that ALLN may be an optimal candidate for the pharmacologic induction of Hsp70. The rapid response, strict selectivity, high magnitude of induction by ALLN, and the possibility of local delivery of this reagent, make its application to clinical medicine promising. Treatment with ALLN may provide an alternative to heat shock for modulation of Hsp70 levels in humans.

ALLN is one of several aldehydic tripeptides that are active against the proteasome (Rock, et al., 1994; Ward, et al, 1995; Lowe, et al., 1995). It can bind and therefore block the active site in the central cavity of proteasome X-ray crystal structure (Lowe, et al., 1995). The demonstration that two other aldehydic tripeptides, ALLM and MG132, and a structurally unique proteasome inhibitor, lactacystin, all induced Hsp70 levels, points to a crucial role for this proteolytic pathway in the regulation of Hsp70 levels in HepG2 cells. Although ALLN and ALLM are potent inhibitors of proteasomes, they also exhibit significant activities against the cysteine proteases, calpain and cathepsin B (Rock, et al., 1994). In contrast, lactacystin is reported to have no detectable effect, even upon extended exposure, on cysteine protease, serine protease, trypsin or chymotrypsin (Ward, et al., 1995, Fenteany, et al., 1995). Overall, the results of experiments with these inhibitors strongly support the conclusion that proteasomes are involved in the induction of Hsp70 synthesis in HepG2 cells.

Inhibition of proteasomal activity may result in induction of Hsp70 synthesis. These results raise the possibility that the link between ALLN and stimulation of both trimerization and activation of HSF1 is a molecule that is sensitive to the status of proteasomal activity. Furthermore, the experiments demonstrating that co-treatment with cycloheximide blocked both the ALLN-associated trimerization of HSF1 (FIG. 6B) and the concomitant increase in hsp72 gene transcription (FIG. 5A) are consistent with the rapid turnover of this molecule. Thus, both de novo protein synthesis and inhibition of proteasomal degradation are required for ALLN to activate HSF1 and thereby induce Hsp70. In contrast to the need for new protein synthesis to see the effects of ALLN, cycloheximide had no effect on heat shock-induced HSF1 activation (FIG. 6B). This is consistent with the report by Mosser et al that the presence of cycloheximide affected neither heat shock-induced hsp70 transcription nor HSF1 DNA-binding activity (Mosser, et al., 1988), and is also consistent with a recent communication (Goodson, et al., 1995) demonstrating that heat treatment can directly convert purified HSF1 from the inactive, monomeric form to the trimeric, DNA binding form in vitro. Based on these findings, it is hypothesized that for responses to stress other than heat shock, a newly synthesized protein that is normally degraded by proteasomes is involved in HSF1 trimerization and activation. When proteasomal degradation is inhibited, the short-lived protein accumulates, HSF1 trimerizes, and Hsp70 synthesis increases. The demonstration that removal of ALLN is associated with a rapid return of hsp72 mRNA and Hsp70 protein levels to baseline supports a key role for a rapidly-turning-over protein. Proteasomal degradation of rapidly turning-over proteins has been demonstrated to be important in regulation of the cell cycle (King, et al., 1995).

The discovery that proteasome inhibitors are potent inducers of Hsp70 is of interest for a number of reasons.

First, the observations presented here imply that a protein normally degraded by proteasomes may be critical for stress responses; identification of this protein will allow for study of the physiological regulation of Hsp70. Second, these results raise the possibility that other ALLN-associated cellular phenomena, such as disruption of cell cycle (Sherwood, et al., 1993), decreased cellular cholesterol ester formation (Schissel, et al., 1995), and inhibition of the degradation of proteins such as apob (41) and HMG-CoA reductase (Inoue, et al., 1991), may be linked to either elevations of Hsp70 levels or inhibition of proteasomal degradation. Finally, it is possible that proteasome inhibitors may be useful as pharmacological inducers of Hsp70 in the clinical arena.

References

Abdella, P. M., P. K. Smith, and P. R. Garfield (1979). A new cleavable reagent for cross-linking and reversible immobilization of proteins. Biochem. Biophys. Res. Commun. 87:734–742.

Angelidis, S. E., I. Lazaridis, and G. N. Pagoulators, (1991) Eur. J. Biochem. 199:35–39.

Ashhurner, M., J. J Bonner, (1979) Cell 17:241–254.

Baler, R., G. Dahl, and R. Voellmy, (1993) Molec. Cell. Biol. 13(4):2486–2496.

Baler, R., W. J. Welch, and R. Voellmy, (1992) J. Cell. Biol. 117: 1151–1159.

Beckmann, R. P., L. A. Mizzen and W. J. Welch, (1990) Science 248:850–854.

Chomczynski, P. and N. Sacchi, (1987) Single-step method of RNA isolation by acid guanidinium thiocyanate-phenolchloroform extraction. Annal. Biochem. 162:156–159.

Craig, E. A. (1985) Crit. Rev. Biochem. 18:239–280.

Craig, E. A., B. K. Baxter, and J. Becker, J. Halladay, and T. Ziegelhotts, (1994) In: "The Biology of Heat Shock Protein and Molecular Chaperone". Cold Spring Harbor Laboratory Press, Cold Spring Harbor, N.Y.

Currie, R. W., M. Karmazyn, M. Kloc, and K. Mailer, (1988) Cir. Res. 63:543–549.

Deshaies, R. J., B. D. Koch M. Werner, E. A. Craig, and R. Schekman, (1988) Nature 332:800–805.

Dierks, T., P. Klappa, and H. Wiech, and R. Zimmermann, (1993) Phil. Trans. R. Soc. Lond. B 79–84.

Dixon, J. L., S. Furukaw, and H. N. Ginsberg, (1991) J. Biol. Chem. 166(8):5080–5086.

Dixon, J. L., H. N. Ginsberg, (1993) J. Lipid Res. 34:167–169.

Fenteany, G., Standaert, R. F., Lane, W. S., Choi, S., Corey, E. J., Schreiber, S. L., (1995) Science 268:726–731.

Freeman, M L., E. Sierra-Rivere, G. Voorhee, D. R. Bisert, and M. J. Meredith, (1993) Synthesis of hsp70 is enhanced in glutathion-depleted HepG2 cells. Radio. Res. 135:387–393.

Gaitanaris, G. A., A. G. Paparassillion, P. Rubock, S. J. Silvertein, and M. E. Gottesman, (1990) Cell 61: 1013–1020.

Gething, M-J. and J. Sambrook, (1992) Nature 355:33–45.

Ginsberg, H. N. (1995) Curr. Opin. Lipidol. 6:275–280.

Goldberg, A. L., Stein, R., Adams, J., (1995) Chem. Biol. 2:503–508.

Goodson, M. L. and Sarge, K. D. (1995) J. Biol. Chem. 270:2447–2450.

Harti, F. U., and J. Martin, (1992) Annu. Rev. Biophys. Biomol. Struct. 21:293–322.

Hayes, S. A. and Dice, J. F. (1996) J. Cell Biol. 132: 255–258.

Hegde, R. S., Zuo, J., Voellmy, R. R., Welch, W. J. (1995) J. Cell Physiol. 165:186–200.

Hightower, L. E. (1991) Cell 66: 191–197.

Hiwasa, T., T. Sanada, S. Sakiyama, (1990) Carcinogenesis 11:75–80.

Inoue, S., S. Bar-Nun, J. Roitelman, and R. D. Simoni, (1991) J. Biol. Chem. 266:13311–13317.

Johnson, A. J., P.A. Berberian, M. Tytell, and M. G. Bond (1995) Arterio. Thromb. Vasc. Biol. 15:27–36.

King, R. W., Peters, J-M., Tugendreich, S., Rolfe, M., Hieter, P., Kirschner, M. (1995) Cell 81:279–288.

Landry, J., P. Chretien, A. Laszlo and H. Lambert, (1991) J. Cell Physiol. 147:93–101.

Li, G.C., L. G. Li, Y. K. Liu, J. Y. Mak, L. Chen, and W. M. Lee (1991) Proc. Natl. Acad. Sci. 88:1681–1685.

Lindquist, S. (1986) Ann. Rev. Biochem. 55:1151–1191.

Liu, A. Y., Z. Lin, H.S. Choi, F. Sorhege, and B. Li, (1989) J. Biol. Chem. 264:12037–12045.

Liu, H., Lightfool. R., Stevens, J. L. (1996) J. Biol. Chem. 271:4805–4812.

Lowe, J., Stock, D., Jap, B., Zwickl, P., Baumeister, W., Huber, R. (1995) Science 268:533–539.

Maniatis T., E. F. Fritsch, and J. Sambrook, (1982) Molecular Cloning: A laboratory manual. Cold Spring Harbor Laboratory. Cold Spring Harbor, N.Y.

Marber, M. S., D. S. Latchman, J. M. Walker, and D. M. Yellon, (1988) Circulation 88:1264–1274.

Marber, M. S., R. Mestril, S. H. Chi, M. R. Sayen, D. M. Yellon, and W. H. Dillmann, (1995) J. Clin. Invest. 95:1446–1456.

Minowada, G., W. J. Welch, (1995) J. Clin. Invest. 95:3–12.

Mitani, K., H. Fujita, Y. Fukuda, A. Kappas, and S. Sassa, (1993) Bioch. J. 290:819–825.

Morimoto, R. I., D. A. Jurivich, P. E. Kroeger, S. K. Mathus, S. P. Murply, A. Nakai, K. Sarge, K. Abravaya, and L. T. Sistonen, In: The Biology of Heat Shock Proteins and Molecular Chaperone, (1994) pp. 417–455. Cold Spring Harbor Laboratory Press. Cold Spring Harbor, N.Y.

Mosser, D. D., N. G. Theodorakis, and R. I. Moromoto, (1988). Coordinate changes in heat shock element-binding activity and Hsp70 gene transcription rates in human cells. Molec. Cell. Biol. 8: 4736–4744.

Neupert, W. and N. Pfanner, (1993) Phil. Trans. R. Soc. Lond. B 355–362.

Ohtsuki, T., M. Matsumoto, K. Kuwabara, K. Kitagana, K. Suzuk, N. Taniguchi, and T. Kamada, (1992) Brain Res. 599:246–254.

Pelham, H. R. B. (1986) Cell 46:959–961.

Plumier, J. L. L., B. M. Ross, R. W. Currie, C. E. Angelidis, H. Kazlaris, G. Kollias, and G. N. Pagoulators, (1995) J. Clin. Invest. 94:1854–1860.

Rabindran, S. K., R. I. Haroun, J. Clos, J. Wisniewski, and C. Wu, (1993). Regulation of heat shock factor trimer formation, role of a conserved leucine zipper. Science 259: 230–234.

Rabindram, S. K., J. Wisniewski, L. Li, G. C. Li, C. Wu (1994) Mol. Cell. Biol. 14:6552–6560.

Rock, L. K., Gramm, C., Rothstein, L., Clark, K., Stein, R., Dick, L., Hwang, D., Goldberg, A. L. (1994) Cell 78: 761–771.

Rodford, N. B., Fina, M., Benjamin, I. J., Moreadith, R. W., Graves, K. H., Zhao, P., Gavva, S., Wiethoff, A., Sherry, A. D., Malloy, C. R., Williams, R. S. (1996) Proc. Natl. Acad. Sci. USA 93:2339–2342.

Sarge, K. D., S. P. Murphy, R. I. Morimoto, (1993) Molec. Cell. Biol. 13(3): 1392–1407.

Sakata, N., X. Wu, J. L. Dixon, and H. N. Ginsberg, (1993) J. Biol. Chem. 268:22967–22970.

Schissel, S. L., Beatini, N., Zha, X., Maxfield, F. R., Tabas, I. (1995) Biochemistry 34:10463–10473.

Schlesinger, M. J., M. Ashbumer, and A. Tissieres, eds (1982). Heat shock: from bacteria to man. Cold Spring Harbor Laboratory, Cold Spring Harbor, N.Y. Sherwood, S. W., A. L. Kung, J. Roitelman, and R. D. Simoni, (1993) Proc. Natl. Acad. Sci. USA 90:3353–3357.

Simon, M. M., A. Reikerstorfer, A. Schwarz, C. Krone, T. A. Luger, M. Jaattela, and T. Schwarz. (1995) J. Clin. Invest. 95:925–933.

Wang, X., R. Sato, M. S. Brown, X. Hua, and J. L. Goldstein, (1994) Cell. 77:53–62.

Ward, C. L., Omura, S., Kopito, R. R., (1995) Cell 83: 121–127.

Welch W. J., and J. R. Feramisco (1984) J. Biol. Chem. 259:4501–4513.

Westwood, J. T., and C. Wu (1993) Molec. Cell. Biol. 13(6):3481–3486.

Zafarullah, M. S. Su, and L. Gedamu, (1993) Exp. Cell. Res.208: 371–377.

Zhou, M. Y., Wu, X. J., Huang, L. S. Ginsberg, H. N. (1995) J. Biol. Chem. 270:25220–25224.

What is claimed is:

1. A method for increasing the level of Heat Shock Protein 70 in a cell which comprises contacting the cell with an effective amount of an inhibitor which inhibits the cysteine protease which cleaves the same bond as the cysteine protease inhibited by N-acetyl-leucyl-leucyl-norleucinal, so as to thereby increase the level of Heat Shock Protein 70 in the cell.

2. A method of claim 1, wherein the Heat Shock Protein 70 is Heat Shock Protein 72.

3. A method of either of claims 1, or 2, wherein the inhibitor is an aldehydic tripeptide.

4. A method of claim 3, wherein the aldehydic tripeptide comprises N-acetyl-leucyl-leucyl-norleucinal or N-acetyl-leucyl-leucyl-methioninal.

5. A method for increasing the level of Heat Shock Protein 70 in a cell which comprises contacting the cell with an effective amount of a proteasome inhibitor which inhibits a proteasome, so as to thereby increase the level of Heat Shock Protein 70 in the cell.

6. A method of claim 5, wherein the proteasome inhibitor is an aldehydic tripeptide.

7. A method of claim 6, wherein the aldehydic tripeptide is selected from the group consisting of N-acetyl-leucyl-leucyl-norleucinal, N-acetyl-leucyl-leucyl-methioninal, and Cbz-leucyl-leucyl-leucinal.

8. A method of claim 5, wherein the proteasome inhibitor is lactacystin.

9. A method for increasing the level of Heat Shock Protein 70 in a subject which comprises administering to the subject an effective amount of an inhibitor which inhibits the cysteine protease which cleaves the same bond as the cysteine protease inhibited by N-acetyl-leucyl-leucyl-norleucinal, so as to thereby increase the level of Heat Shock Protein 70 in the subject.

10. A method for increasing the level of Heat Shock Protein 70 in a subject which comprises administering to the subject an effective amount of a pharmaceutical composition comprising an effective amount of an inhibitor which inhibits the cysteine protease which cleaves the same bond as the cysteine protease inhibited by N-acetyl-leucyl-leucyl-norleucinal, and a pharmaceutically acceptable carrier, so as to thereby increase the level of Heat Shock Protein 70 in the subject.

11. A method of either of claims 9 or 10, wherein the Heat Shock Protein 70 is Heat Shock Protein 72.

12. A method of either of claims 9 or 10, wherein the inhibitor is an aldehydic tripeptide.

13. A method of claim 12, wherein the aldehydic tripeptide comprises N-acetyl-leucyl-leucyl-norleucinal or N-acetyl-leucyl-leucyl-methioninal.

14. The method of either of claims 9 or 10, wherein the subject is a mammal.

15. The method of either of claims 9 or 10, wherein the subject is a human.

16. A method for increasing the level of Heat Shock Protein 70 in a subject which comprises administering to the subject an effective amount of an inhibitor which inhibits a proteasome, so as to thereby increase the level of Heat Shock Protein 70 in the subject.

17. A method of claim 16, wherein the Heat Shock Protein 70 is Heat Shock Protein 72 .

18. A method of claim 16, wherein the proteasome inhibitor is an aldehydic tripeptide.

19. A method of claim 18, wherein the aldehydic tripeptide is selected from the group consisting of N-acetyl-leucyl-leucyl-norleucinal, N-acetyl-leucyl-leucyl-methioninal, and Cbz-leucyl-leucyl-leucinal.

20. A method of claim 16, wherein the proteasome inhibitor is lactacystin.

21. The method of any one of claims 16, 17, 18, 19, 20, wherein the subject is a mammal.

22. The method of any one of claims 16, 17, 18, 19, or 20, wherein the subject is a human.

* * * * *